(12) United States Patent
Seo et al.

(10) Patent No.: US 9,365,691 B2
(45) Date of Patent: Jun. 14, 2016

(54) FABRICATING POROUS MATERIALS USING INTREPENETRATING INORGANIC-ORGANIC COMPOSITE GELS

(75) Inventors: Dong-Kyun Seo, Chandler, AZ (US); Alex Volosin, Tempe, AZ (US)

(73) Assignee: ARIZONA BOARD OF REGENTS, A BODY CORPORATE OF THE STATE OF ARIZONA ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 315 days.

(21) Appl. No.: 13/814,031

(22) PCT Filed: Aug. 3, 2011

(86) PCT No.: PCT/US2011/046381
§ 371 (c)(1),
(2), (4) Date: Feb. 27, 2013

(87) PCT Pub. No.: WO2012/018890
PCT Pub. Date: Feb. 9, 2012

(65) Prior Publication Data
US 2013/0153830 A1    Jun. 20, 2013

Related U.S. Application Data

(60) Provisional application No. 61/371,428, filed on Aug. 6, 2010.

(51) Int. Cl.
*C08J 9/00* (2006.01)
*C08J 3/075* (2006.01)
(Continued)

(52) U.S. Cl.
CPC . *C08J 9/00* (2013.01); *C01B 13/32* (2013.01); *C01B 31/02* (2013.01); *C01F 7/34* (2013.01);
(Continued)

(58) Field of Classification Search
None
See application file for complete search history.

(56) References Cited

U.S. PATENT DOCUMENTS 3,558,273 A    1/1971    Beck
4,374,232 A    2/1983    Davis
(Continued)

FOREIGN PATENT DOCUMENTS

EP    0013497    7/1980
EP    0454239    10/1991
(Continued)

OTHER PUBLICATIONS

Bauman et al., "Synthesis of High-Surface-Area Alumina Aerogels without the Use of Alkoxide Precursors", Chem. Mater. 17, pp. 395-401 (2005).
(Continued)

*Primary Examiner* — Harold Pyon
*Assistant Examiner* — Katie L Hammer
(74) *Attorney, Agent, or Firm* — Fish & Richardson P.C.

(57) ABSTRACT

Porous materials are fabricated using interpenetrating inorganic-organic composite gels. A mixture or precursor solution including an inorganic gel precursor, an organic polymer gel precursor, and a solvent is treated to form an inorganic wet gel including the organic polymer gel precursor and the solvent. The inorganic wet gel is then treated to form a composite wet gel including an organic polymer network in the body of the inorganic wet gel, producing an interpenetrating inorganic-organic composite gel. The composite wet gel is dried to form a composite material including the organic polymer network and an inorganic network component. The composite material can be treated further to form a porous composite material, a porous polymer or polymer composite, a porous metal oxide, and other porous materials.

21 Claims, 27 Drawing Sheets

(51) Int. Cl.

| | |
|---|---|
| *C01B 13/32* | (2006.01) |
| *C01B 31/02* | (2006.01) |
| *C01F 7/34* | (2006.01) |
| *C01G 19/02* | (2006.01) |
| *C01G 25/02* | (2006.01) |
| *C01G 30/00* | (2006.01) |
| *C07F 9/90* | (2006.01) |
| *C07F 5/06* | (2006.01) |
| *C07F 7/00* | (2006.01) |

(52) U.S. Cl.
CPC ............... *C01G 19/02* (2013.01); *C01G 25/02* (2013.01); *C01G 30/004* (2013.01); *C07F 5/068* (2013.01); *C07F 7/003* (2013.01); *C07F 7/006* (2013.01); *C07F 9/902* (2013.01); *C08J 3/075* (2013.01); *C01P 2002/54* (2013.01); *C01P 2002/72* (2013.01); *C01P 2002/84* (2013.01); *C01P 2004/04* (2013.01); *C01P 2006/12* (2013.01); *C01P 2006/14* (2013.01); *C01P 2006/16* (2013.01); *C08J 2361/00* (2013.01)

(56) References Cited

U.S. PATENT DOCUMENTS

| | | | |
|---|---|---|---|
| 4,923,830 | A | 5/1990 | Everhart et al. |
| 5,045,511 | A | 9/1991 | Bosomworth et al. |
| 5,244,726 | A | 9/1993 | Laney et al. |
| 5,342,595 | A | 8/1994 | Davidovits et al. |
| 5,680,713 | A | 10/1997 | Forbert et al. |
| 5,725,836 | A | 3/1998 | Rouanet et al. |
| 6,131,305 | A | 10/2000 | Forbert et al. |
| 6,187,248 | B1 | 2/2001 | O'Neill et al. |
| 6,254,845 | B1 | 7/2001 | Ohashi et al. |
| 6,642,285 | B1 | 11/2003 | Bohner |
| 6,699,808 | B1 | 3/2004 | Schwertfeger et al. |
| 6,893,564 | B2 | 5/2005 | Mueller et al. |
| 7,297,321 | B2 | 11/2007 | Shpeizer et al. |
| 7,456,123 | B2 | 11/2008 | Wachter |
| 7,771,686 | B2 | 8/2010 | Safoe-crentsil et al. |
| 8,557,214 | B2 | 10/2013 | Seo |
| 9,242,900 | B2 | 1/2016 | Seo et al. |
| 2001/0023296 | A1 | 9/2001 | Kato et al. |
| 2003/0108785 | A1 | 6/2003 | Wu et al. |
| 2004/0047798 | A1* | 3/2004 | Oh et al. ............ 423/414 |
| 2004/0258611 | A1 | 12/2004 | Barrow |
| 2005/0152829 | A1 | 7/2005 | Shpeizer et al. |
| 2005/0272593 | A1 | 12/2005 | Wachter |
| 2006/0057355 | A1* | 3/2006 | Suzuki et al. ............ 428/308.4 |
| 2006/0292054 | A1 | 12/2006 | Chaumonnot et al. |
| 2007/0003749 | A1 | 1/2007 | Asgari |
| 2007/0009689 | A1 | 1/2007 | Murer |
| 2007/0048605 | A1 | 3/2007 | Pez et al. |
| 2007/0125271 | A1 | 6/2007 | Barlet-Gouedard et al. |
| 2007/0125272 | A1 | 6/2007 | Johnson |
| 2007/0128491 | A1 | 6/2007 | Chisholm et al. |
| 2007/0259979 | A1* | 11/2007 | Lee ............ 521/64 |
| 2008/0028994 | A1 | 2/2008 | Barlet-Gouedard et al. |
| 2008/0028995 | A1 | 2/2008 | Barlet-Gouedard et al. |
| 2008/0067149 | A1 | 3/2008 | Piesslinger-Schweiger et al. |
| 2008/0090716 | A1 | 4/2008 | Cherepy et al. |
| 2008/0226893 | A1 | 9/2008 | Yang et al. |
| 2009/0026413 | A1 | 1/2009 | Patoux et al. |
| 2009/0041653 | A1 | 2/2009 | Hwang et al. |
| 2009/0256262 | A1 | 10/2009 | Farnworth et al. |
| 2009/0288557 | A1 | 11/2009 | Carati et al. |
| 2010/0104500 | A1 | 4/2010 | Holland |
| 2010/0222204 | A1 | 9/2010 | Frizon et al. |
| 2011/0092363 | A1 | 4/2011 | Seo et al. |
| 2012/0007020 | A1 | 1/2012 | Tarascon et al. |
| 2012/0235073 | A1 | 9/2012 | Seo et al. |
| 2013/0055924 | A1 | 3/2013 | Seo et al. |

FOREIGN PATENT DOCUMENTS

| | | |
|---|---|---|
| EP | 0497966 | 8/1992 |
| EP | 497466 | 8/1995 |
| EP | 1230008 | 8/2002 |
| JP | 2003206112 | 7/2003 |
| KR | 10-2001-0082910 | 8/2001 |
| KR | 10-2001-0107049 | 12/2001 |
| WO | 99/32218 | 7/1999 |
| WO | 01/28675 | 4/2001 |
| WO | WO2004018090 | 4/2004 |
| WO | WO2005019130 | 3/2005 |
| WO | WO2005054340 | 6/2005 |
| WO | 2007/064053 | 6/2007 |
| WO | 2007/129991 | 11/2007 |
| WO | 2008/124343 | 10/2008 |
| WO | 2009/050196 | 4/2009 |
| WO | 2009/140030 | 11/2009 |
| WO | WO2011046910 | 4/2011 |
| WO | WO2011068830 | 6/2011 |
| WO | WO2012018890 | 2/2012 |

OTHER PUBLICATIONS

Aguado-Serrano et al., "Silica/C composites prepared by the sol-gel method. Influence of the synthesis parameters on textural characteristics", Microporous and Mesoporous Materials. 74, pp. 111-119 (2004).

Aguado-Serrano et al., "Surface and catalytic properties of acid metal—carbons prepared by the sol-gel method", Applied Surface Science. 252, pp. 6075-6079 (2006).

Bell et al., "Nano- and Microporosity in Geopolymer Gels", Microsc Microanal . 12, pp. 552-553 (2006).

Boettcher et al., "Harnessing the Sol-Gel Process for the Assembly of Non-Silicate Mesostructured Oxide Materials", Acc. Chem. Res. 40, pp. 784-792 (2007).

Boffa et al., "Preparation of templated mesoporous silica membranes on macroporous a-alumina supports via direct coating of thixotropic polymeric sols", Microporous and Mesoporous Materials. 100, pp. 173-182 (2007).

Bruno et al., "Characterization of monolithic porous carbon prepared from resorcinol/formaldehyde gels with cationic surfactant", Colloids and Surfaces A: Physicochemical and Engineering Aspects. 358, pp. 13-30 (2010).

Capadona et al., "A versatile approach for the processing of polymer nanocomposites with selfassembled nanofibre templates", Nature Nanotechnology. 2, pp. 765-769 (2007).

Duxson et al., "Geopolymer technology: the current state of the art", J Mater. Sci. 42, pp. 2917-2933 (2007).

Han et al., "The effect of silica template structure on the pore structure of mesoporous carbons", School of Chemical Engineering, Seoul National University, Carbon. 41, pp. 1049-1056 (2003).

Iancu et al., "Low-temperature synthetic method for size-controlled CdSe nanocrystals: utilization of boron selenide", Chem. Commun. 20, pp. 2298-2299 (2004).

Dong-Ying et al., "Low-temperature sintering method for NiCuZn ferrite and effect of Mn addition on electromagnetic properties", Trans. Nonferrous Met. Soc. China. 16, pp. 67-70 (2006).

Komnitsas et al., "Geopolymerisation: A review and prospects for the minerals industry", Minerals Engineering, 20, pp. 1261-1277 (2007).

Kubel et al., "Recent Advances in Electron Tomography: TEM and HAADF-STEM Tomography for Materials Science and Semiconductor Applications", Microsc. Microanal. 11, pp. 378-400 (2005).

Kwak et al., "Penta-coordinated Al3+ ions as preferential nucleation sites for BaO on γ-Al2O3: An ultra-high-magnetic field 27Al MAS NMR study", Journal of Catalysis, 251, pp. 189-194 (2007).

Laine et al., "Making Nanosized Oxide Powders from Precursors by Flame Spray Pyrolysis", Key Engineering Materials, 159-160, pp. 17-24 (1999).

Lee et al., "Recent Progress in the Synthesis of Porous Carbon Materials", Advanced Materials. 18, pp. 2073-2094 (2006).

Leventis et al., "One-Pot Synthesis of Interpenetrating Inorganic/Organic Networks of CuO/Resorcinol-Formaldehyde Aerogels: Nanostructured Energetic Materials", J. Am. Chem. Soc. 131, pp. 4576-4577 (2009).

(56) References Cited

OTHER PUBLICATIONS

Mahata et al., "Combustion synthesis of gadolinia doped ceria powder", Journal of Alloys and Compounds, 391, pp. 129-135 (2005).
Moreno-Castilla et al., "Synthesis and surface characteristics of silica- and alumina-carbon composite xerogels", Phys. Chem. Chem. Phys. 2, pp. 4818-4822 (2000).
Morris et al., "Silica Sol as a Nanoglue: Flexible Synthesis of Composite Aerogels", Science, 284, pp. 622-624 (1999).
Mulik et al., "Time-Efficient Acid-Catalyzed Synthesis of Resorcinol-Formaldehyde Aerogels", Chem. Mater.19, pp. 6138-6144 (2007).
Nedelec et al., "Sol-Gel Processing of Nanostructured Inorganic Scintillating Materials", Journal of Nanomaterials, 2007, pp. 1-8 (2007).
Pek et al., "A thixotropic nanocomposite gel for three-dimensional cell culture", Nature Nanotechnology, 3, pp. 671-675 (2008).
Provis et al., "Do Geopolymers Actually Contain Nanocrystalline Zeolites? A Reexamination of Existing Results", Chem. Mater., 17, pp. 3075-3085 (2005).
Richards et al., "Consolidation of Metal Oxide Nanocrystals. Reactive Pellets with Controllable Pore Structure That Represent a New Family of Porous, Inorganic Materials", J. Am. Chem. Soc. 122, pp. 4921-4925 (2000).
Rolison et al., "Electrically conductive oxide aerogels: new materials in electrochemistry", J. Mater. Chem. 11, pp. 963-980 (2001).
Schuyten et al., "A Novel Combustion Synthesis Preparation of CuO/ZnO/ZrO2/Pd for Oxidative Hydrogen Production from Methanol", Catal Lett. 121, pp. 189-198 (2008).
Sivashanmugam et al., "Glycine-Assisted Sol-Gel Combustion Synthesis and Characterization of Aluminum-Doped LiNiVO4 for Use in Lithium-Ion Batteries", Journal of the Electrochemical Society, 153, pp. A497-A503 (2006).
Thomas et al., "Amorphous Zeolites", Angewandte Chemie International Edition in English, 19, pp. 745-746 (1980).
Villemin et al., "A one step process for grafting organic pendants on alumina via the reaction of alumina and phosphonate under microwave irradiation", Chem. Commun. 2001, pp. 2060-2061 (2001).
Zhang et al., "Mesostructured Forms of γ-Al2O3", J. Am. Chem. Soc. 124, pp. 1592-1593 (2002).
Zurner et al., "Visualizing single-molecule diffusion in mesoporous materials", Nature, 450, pp. 708-708 (2007).
Joseph Davidovits, "Geopolymer Chemistry and Applications", Jun. 2008, Chapter 1, 17 pages.
Dr. Lynn A. Capadona et al., "X-Aerogel Processing Time Reduced by One-Pot Synthesis," Dec. 14, 2007, retrieved from http://www.grc.nasa.gov/WWW/RT/2006/RX/RX20P-capadona1.html, downloaded on Jul. 26, 2013, 4 pages.
Authorized Officer Tae Kwang Jung, International Search Report and Written Opinion dated Apr. 6, 2012 for PCT Application No. PCT/US2011/046381, 11 pages.
W. M. Kriven, "Inorganic Polysialates or 'Geopolymers'" American Ceramic Society Bulletin, May 2010, vol. 89, No. 4, pp. 31-34.
Kriven et al., "Microstructure and nanoporosity of as-set geopolymers" Ceramic Engineering and Science Proceedings 2007, vol. 27, Issue 2, pp. 491-503.
Joseph Davidovits, Geopolymer Chemistry and Applications, 3rd Edition, Jul. 2011, pp. 1-33.
A. S. Wagh, "Chemically Bonded Phosphate Ceramics—A Novel Class of Geopolymers," Ceramic Transactions 2005, vol. 165, 12 pages.
J. Aleman et al., "Definitions of Terms Relating to the Structure and Processing of Sols, Gels, Networks, and Inorganic—Organic Hybrid Materials," Pure and Applied Chemistry, vol. 79, No. 1, 2007, pp. 1801-1829.
Robert L. Burwell, Jr. "Manual of Symbols and Terminology for Physicochemical Quantities and Units—Appendix II. Definitions, Terminology and Symbols in Colloid and Surface Chemistry. Part II: Heterogeneous Catalysis," Pure and Applied Chemistry, vol. 46, 1976, pp. 71-90.
C. H. Christensen et al., "Mesoporous zeolite single crystal catalysts: Diffusion and catalysis in hierarchical zeolites" Catalysis Today 128, 2007, pp. 117-122.
L. Gueudré et al, "Diffusion in zeolites: is surface resistance a critical parameter?" Adsorption 16, 2010, pp. 17-27.
A. L. Mayers et al., "Thermodynamics of Mixed-Gas Adsorption" A.I.Ch.E. Journal, vol. 11, No. 1, Jan. 1965, pp. 121-127.
Gresham, Dr. Robert M., contributing editor, "Viscosity: A fluid's resistance to flow," Tribology & Lubrication Technology, Nov. 2008, pp. 55-57.
Le-Ping L et al, "Preparation phosphoric acid-based porous geopolymers," Applied Clay Science, vol. 50, No. 4, Dec. 1, 2010, pp. 600-603.

* cited by examiner

FABRICATING POROUS MATERIALS USING INTREPENETRATING INORGANIC-ORGANIC COMPOSITE GELS

CROSS-REFERENCE TO RELATED APPLICATIONS

This application is a U.S. National Phase Application of International Patent Application No. PCT/US2011/046381 filed Aug. 3, 2011, which claims priority to U.S. Application Ser. No. 61/371,428, filed on Aug. 6, 2010, both of which are incorporated herein by reference in their entirety.

STATEMENT OF GOVERNMENT INTEREST

This work was supported by the Center for Bio-Inspired Solar Fuel Production, an Energy Frontier Research Center funded by the U.S. Department of Energy, Office of Science, Office of Basic Energy Sciences under Award Number DE-SC0001016. The government has certain rights in the invention.

TECHNICAL FIELD

This application relates to porous materials.

BACKGROUND

Porous materials find application in modern technologies including thermal insulation, gas storage, active membranes, fuel cells, solar cells, batteries, supercapacitors, drug delivery, bio-implants, sensors, photonics, water purification, and the like, owing to their high surface area and porosity. Examples include porous metal oxides, organic polymers, and carbon, as well as composites thereof.

Nanoporous materials, for example, having a pore distribution in the nanometer range, can be synthesized by a template method or a solvent removal method.

In the template method, sacrificial templates can be mixed into a liquid body of the precursor that polymerizes to form a solid. Then, the templates can be removed to leave pore space in the solid body. The templates can be organic polymers, self-assemblies of surfactants, or other nanoparticulate matter. In some cases, the sacrificial templates can be a pre-formed bulk porous solid. In such cases, the porous body can be infiltrated by the liquid precursor by soaking the body in the liquid. For example, porous carbon can be produced by infiltrating chromatography-grade porous silica with a solution of phenol, formaldehyde, and tetraethylammonium hydroxide; polymerizing the phenol and formaldehyde in the pores of silica; pyrolyzing and carbonizing the polymer; and etching the silica out from the material, as described in U.S. Pat. No. 4,263,268, entitled "Preparation of Porous Carbon," to Knox et al., which is incorporated herein by reference. The tetraethylammonium hydroxide acts as a catalyst for the polymerization of phenol and formaldehyde.

The solvent removal method can start with formation of a wet gel. In a wet gel, the solid component is formed by "sol" nanoparticles that are held together loosely but continuously throughout the entire body of the gel. The solvent can be removed, for example, by drying, to leave a porous material. The porosities and the pore morphologies of the resulting materials can be affected by the liquid removal methods such as heating, ambient drying, supercritical drying, cryogenic drying, and the like. The gels can be made of various materials including oxygen-containing metal compounds and organic polymers. Pyrolytic polymer gels can be carbonized to form porous carbon.

In some cases, the wet gel can be an "interpenetrating" inorganic-organic composite gel. The subsequent pore liquid removal can provide a porous composite material made of different compounds. In certain cases, interpenetrating inorganic-organic composite gels are prepared by starting with a wet gel that has only one solid network component, inorganic or organic. Through a solvent exchange process, the pore liquid of the wet gel is replaced by another liquid that includes the precursors for the other network component. This method can be time-consuming and can require excessive precursor chemicals.

U.S. Patent Application Publication No. 2010/052276 entitled "Fabricating porous materials using thixotropic gels," to D.-K. Seo and A. Volosin, which is incorporated by reference herein, shows that interpenetrating inorganic-organic composite gels can be prepared by first preparing an inorganic thixotropic gel such as alumina gel. A solution of organic polymer precursors is added to the thixotropic gel, while the gel is sheared and thus becomes liquefied. Upon removing the shear, the material gels again with the organic polymer precursors in the pore liquid.

In other cases, inorganic gel precursors and organic polymer gel precursors are premixed first in a solvent and then an interpenetrating inorganic-organic gel is formed by promoting "simultaneous" gelation of both inorganic gel precursors and organic polymer gel precursors in the solution. In U.S. Pat. No. 5,254,638, entitled "Composite materials of interpenetrating inorganic and organic polymer networks," to B. M. Novak et al., which is incorporated herein by reference, interpenetrating networks of silica (or titania) and polymerized alcohols are reported to form through hydrolysis of alkoxides of silicon (or titanium), polycondensation of the hydrolyzed alkoxides and polymerization of alcohols. The hydrolysis, polycondensation, and polymerization occur "concurrently" in a solution and are catalyzed by a common acid that is added to the solution together with the precursors. The composite gels are then supercritically dried to form composite aerogels. It is noted that these co-gelation methods are different from other procedures for porous inorganic-organic composites that are based on "copolymerization" between inorganic and organic gel precursors. [See for example, C. Moreno-Castilla and F. J. Maldonado-Hódar, "Synthesis and surface characteristics of silica- and alumina-carbon composite xerogels" *Phys. Chem. Chem. Phys.* 2000, 2, 4818, which is incorporated herein by reference].

Such co-gelation methods have been reported for metal oxides other than silica or titania in preparation of porous interpenetrating metal oxide-polymer composites. Polymerization of certain organic gel precursors such as resorcinol-formaldehyde pair can be catalyzed by either an acid or a base. Some inorganic salts are acidic in water and thus can act as both an acid catalyst for the organic polymerization and a source for metal oxide in the final product. For example, N. Leventis et al. has shown that CuO/resorcinol-formaldehyde gels can be prepared by two sol-gel processes running "concurrently" in a mixture of $CuCl_2 \cdot xH_2O$, resorcinol, formaldehyde, and epichlorohydrin in an $H_2O$/DMSO solvent at 80° C. for 4 hours. [See N. Leventis et al., "One-pot synthesis of interpenetrating inorganic/organic networks of CuO/resorcinol-formaldehyde aerogels: nanostructured energetic materials" *J. Am. Chem. Soc.* 2009, 131, 4576, which is incorporated by reference herein.] In their work, the CuO precursor, $CuCl_2 \cdot xH_2O$, was shown to be acidic (pH~3) in the $H_2O$/DMSO solvent, and the acid catalyzed the polymerization of the resorcinol and formaldehyde. The CuO/resorcinol-formaldehyde gels were supercritically dried to provide CuO/resorcinol-formaldehyde composite aerogels.

In some cases, it is unclear whether or not both the inorganic and the organic components form network structures throughout the solution in "concurrent gelation" methods. For example, the work by R. Vendamme et al. on preparation of zirconia-polymer composite membranes raises the problem and indicates that their porous membranes may have "partial" networks of zirconia instead of "continuous" networks. [See R. Vendamme et al., "Robust free-standing nanomembranes of organic/inorganic interpenetrating networks" Nature Mater. 2006, 5, 494, which is incorporated herein by reference.]

In some cases, the network structures are used further to fabricate a new porous material by removing either the inorganic or the organic network component. For example, removal of the metal oxide component from a porous interpenetrating metal oxide-carbon composite will provide a porous carbon, and removal of the carbon component from a porous interpenetrating metal oxide-carbon composite will provide a porous metal oxide. If one of the network components is not sufficiently continuous, the porous material from the removal of the other component may not be continuous, either. In addition, a "partial" or incomplete network component can be harder to etch out when it is fully surrounded by the other network component and thus less easily accessed by an etching agent. Furthermore, if the material is used as an electrical conduction medium, the resulting porous material may be less conductive at least in part because of the partially continuous network structure.

SUMMARY

This specification describes technologies relating to fabricating porous materials using interpenetrating inorganic-organic composite gels and the fabricated porous materials. The inorganic network component may be substantially free from silica or substantially free from silicon-containing compounds. The interpenetrating inorganic-organic composite gels include an inorganic network component and an organic polymer network component that interpenetrate each other.

In one aspect, preparing a material includes providing a mixture or precursor solution including an inorganic gel precursor, an organic polymer gel precursor, and a solvent. The precursor solution is treated to form an inorganic wet gel including an inorganic metal oxide gel network and a liquid including the organic polymer gel precursor and the solvent. The inorganic wet gel is treated to form an organic polymer network in its body (i.e., in the inorganic wet gel). In some implementations, the organic polymer gel precursor may partially undergo polymerization during the inorganic wet gel formation. The subsequent treatment of the inorganic wet gel may make the polymerization more complete. This provides a composite wet gel that includes both inorganic and organic network components. The inorganic-organic composite wet gel is dried (e.g., the liquid component is removed from the composite wet gel) to form the material. The material is a composite material that may be porous. The material may be treated to remove at least one component, thereby yielding another material (e.g., another porous material).

In another aspect, preparing a material includes treating a mixture or precursor solution including an inorganic gel precursor, an organic polymer gel precursor, and a solvent to form an inorganic wet gel including the organic polymer gel precursor and the solvent. The inorganic wet gel is treated to form a composite wet gel including an organic polymer network in the inorganic wet gel. The composite wet gel is dried to form a composite material including the organic polymer network and an inorganic network component. The composite material may be a porous material.

Implementations may include one or more of the following features. In some implementations, the precursor solution includes one or more additives selected from the group consisting of fibers, woven fibers, particles, carbon veils, carbon fibers, viscosity modifiers, polymers, and additional porous materials. The inorganic gel precursor can include one or more additives selected from the group consisting of: compounds including a metal, semimetal, metalloid or semiconductor; inorganic salts; acid scavengers; epoxy-containing compounds; urea; organometallic compounds; and alkoxides of metals, semi-metals, metalloids, and/or semi-conductors. The organic polymer gel precursor can include one or more additives selected from the group consisting of carbon-containing compounds, resorcinol, formaldehyde, phenol, polymerizable carbon-containing compounds, hydroxyl-substituted benzenes, urea, diamines, sugars, furfuryl alcohol, cellulose, and mesophase pitch. The inorganic wet gel can include one or more additives selected from the group consisting of oxides, hydroxides, alkoxides, oxohydroxides, oxoalkoxides, oxo salts, oxo salt hydrates of a metal, semi-metal, metalloid, or semi-conductor, or hydrated forms of metal oxides that acts as a solid acid catalyst or solid base catalyst for the organic polymer network.

Treating the precursor solution can include heating the precursor solution to a temperature up to about 50° C. In some implementations, the organic polymer gel precursors are polymerized to form the organic polymer network in the presence of an acid, a base, an oxidizing agent, a reducing agent, a base, or any combination thereof and/or wherein the organic polymer gel precursors are polymerized to form the organic polymer network by thermal polymerization, radical polymerization, photocatalytic polymerization, and/or thermobaric polymerization, and/or wherein the organic polymer precursors are polymerized to form the organic polymer network with microwave radiation.

Treating the inorganic wet gel can include treating the inorganic wet gel at a temperature higher than the temperature employed for treating the precursor solution and/or heating the inorganic wet gel to a temperature greater than about 50° C.

Drying the composite wet gel can include supercritical drying, cryogenic drying, heating, or the like. The drying may yield a composite xerogel which may have a porosity lower than that expected from supercritical drying or cryogenic drying. In some implementations, the heating can cause dehydration, decomposition, combustion, or pyrolysis of a part of the solid component of the composite wet gel.

In some implementations, preparing a porous and/or composite material including metal oxide, semi-metal oxide, metalloid oxide, or semi-conductor oxide and an organic polymer includes providing a mixture of one or more inorganic gel precursors, one or more organic polymer gel precursors, and one or more solvents. The mixture is then treated to form a wet gel including a liquid and an inorganic network component. The wet gel is then treated to form an organic polymer gel network in its body, and the liquid component of the wet gel is removed.

In some cases, materials including non-silicate inorganic oxide and an organic polymer are prepared. The method includes providing a mixture of one or more inorganic salts, one or more acid scavengers, one or more organic polymer gel precursors, and one or more solvents. The mixture is treated to form a wet gel including a non-silicate inorganic oxide network component. The wet gel is then treated to form an organic polymer gel network in its body, and the liquid component of the wet gel is removed. At least one among the inorganic salts is chosen to be acidic in water. The acid scavengers can include epoxy-containing organic compounds such as ethylene oxide, propylene oxide, and epichlorohydrin; organic compounds such as urea that become basic upon hydrolysis; inorganic bases such as ammonium hydroxide, or a combination thereof.

The metal oxide network component can be, for example, an oxide, hydroxide, alkoxide, oxohydroxide, oxoalkoxide, oxo salt, oxo salt hydrate of a metal, semi-metal, metalloid, or semi-conductor, or a hydrated form of a metal oxide. In some implementations, the gel can be formed in a sol-gel process. In some cases, the gel can be formed by precipitation from a solution.

In some implementations, the oxygen-containing metal compound may act as a catalyst for the polymerization of the organic polymer gel precursors. In some cases, inorganic gel networks have M-OH hydroxyl groups on the surface which are Brönsted acid sites and can promote polymerization.

The composite materials can be treated further. In certain implementations, the composite materials are treated to remove one component and thus to produce a porous (or another porous) material. In some cases, treating the composite material includes heating the composite material in an excess of oxygen to burn off the organic polymer network to form a porous metal oxide substantially free from the organic polymer network. In other cases, treating the composite material includes etching out the inorganic network component to form a porous organic polymer substantially free from the inorganic network component.

In some implementations, the composite materials are heated with a limited amount of oxygen and thus the polymer component is pyrolyzed to produce a porous metal oxide-carbon composite material. In some cases, the metal oxide component undergoes a carbothermal reaction to yield porous carbon embedded with metal particles inside. In some cases, the pyrolysis can be carried out with a sufficient amount of oxygen to produce a porous metal oxide-carbon composite material with a discontinuous carbon network (e.g., a metal oxide network with discrete regions including carbon-containing polymer components). In some cases, the porous metal oxide-carbon composite material is treated further. For example, the porous metal oxide-carbon composite material can be heated with an excess of oxygen to burn off the carbon and form a porous metal oxide. Some implementations include contacting the porous metal oxide-carbon composite with a solvent to etch the metal oxide out and form a porous carbon.

In some cases, the composite material is heated with a sufficient amount of oxygen to remove the organic polymer network or some or all of the carbon, thereby yielding a porous metal oxide (e.g., substantially free from the organic polymer network or substantially free from carbon, respectively). The porous metal oxide can be conducting or semi-conducting. In some cases, the porous metal oxide can be a transparent conducting oxide. The composite material can be heated in a limited oxygen environment to yield a porous composite including a metal oxide and carbon. In certain cases, the porous composite is treated to remove the metal oxide, thereby yielding a porous carbon or porous carbon composite substantially free from the metal oxide. Treating the porous composite may include etching out the metal oxide with an acid or a base, and dissolving or decomposing the metal oxide. The porous composite can be treated to remove some or all of the inorganic network component, thereby yielding a porous polymer or porous polymer composite. Treating the porous composite can include etching out the inorganic network component with an acid or base, and dissolving or decomposing the inorganic network component.

In some implementations, another component can be removed from the composite material to form another porous and/or composite material. In some cases, the porous and/or composite materials can be used as a reagent or component to form a new material. In certain cases, the process of preparing the porous and/or composite material can be applied more than once to the same material to form a heterogeneous composite structure. Examples of the heterogeneous composite structures include a core/shell structure and a multi-layer structure. The porous and/or composite materials can be nanoporous, hierarchically porous, or in the form of monoliths, films, plates, coatings, powders, particulates, or any combination thereof. In some cases, the porous and/or composite materials are conducting or semi-conducting. In certain cases, the porous and/or composite materials are transparent or semi-transparent.

The details of one or more implementations of the specification are set forth in the accompanying drawings and the description below. Other features, aspects, and advantages of the specification will become apparent from the description, the drawings, and the claims.

DESCRIPTION OF THE DRAWINGS

FIG. 14 is a transmission electron micrograph of porous antimony-doped tin oxide (sample 3a) formed by the method described in Example 3a.

DETAILED DESCRIPTION

Methods for fabricating porous materials using interpenetrating inorganic-organic composite gels are described. As used herein, an "interpenetrating inorganic-organic composite gel" is a gel that includes an inorganic network component and an organic gel network component that interpenetrate each other. Furthermore, methods for fabricating new porous materials by removing substantially all of the inorganic network component or substantially all the organic network component from the formed interpenetrating inorganic-organic composite gels are described. The inorganic network component can include at least one oxygen-containing metal compound. As used herein, "metal" generally refers to a metal, semi-metal, metalloid, or semi-conductor. As used herein, "oxygen-containing metal compound," "inorganic network component," "inorganic oxide network component," and "metal oxide network component" generally refer to a metal oxide, metal oxyhydroxide, metal hydroxide, metal alkoxide, or metal oxoalkoxide. The oxygen-containing metal compound, inorganic network component, inorganic oxide network component, or metal oxide network component can be an oxide, hydroxide, alkoxide, oxohydroxide, oxoalkoxide, oxo salt, oxo salt hydrate of a metal, semi-metal, metalloid, or semi-conductor, or a hydrated form of a metal oxide. An organic network component can include an organic polymer or a carbon-containing polymer.

Figure 1A:
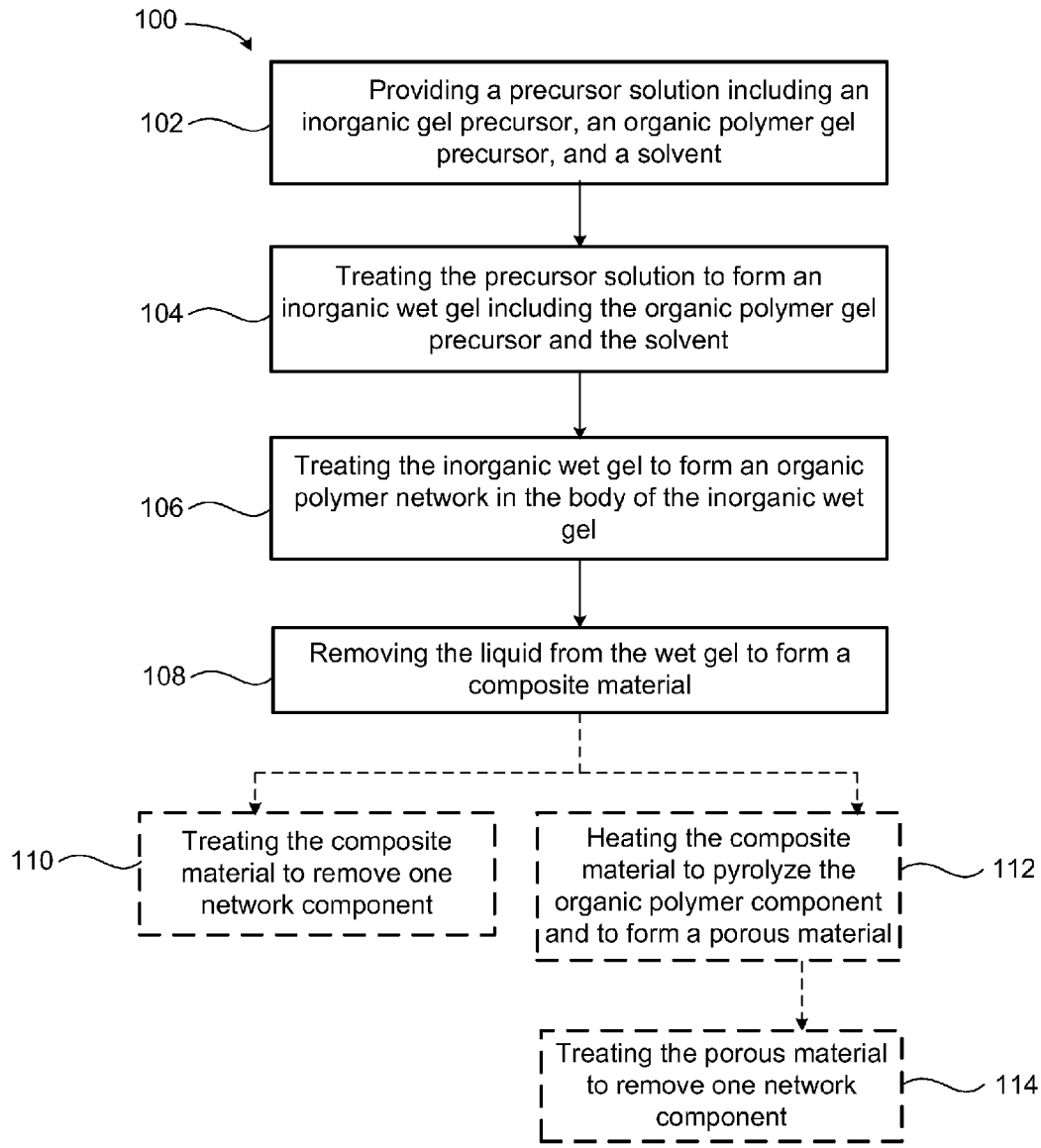
FIG. 1A and FIG. 1B are flow charts that depict methods for forming porous materials.

Referring to FIG. 1, a process for preparing porous materials 100 includes providing a mixture including an inorganic gel precursor, an organic polymer gel precursor, and a solvent, as shown in operation 102. In some cases, the inorganic gel precursor includes at least one metal element. In certain cases, the inorganic gel precursor includes one or more inorganic salts, organometallic compounds, or alkoxides of metals, semi-metals, metalloids, and/or semi-conductors such as Li, Na, K, Rb, Cs, Be, Mg, Ca, Sr, Ba, B, Al, Ga, In, Si, Ge, Sn, Pb, P, As, Sb, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, Sc, Y, Lu, La, Ce, Pr, Nd, Sm, Eu, Gd, Tb, Dy, Ho, Er, Tm, Yb, Th, U, Tl, Pb, Bi, or any combination thereof. Exemplary inorganic salts include aluminum chloride hexahydrate, aluminum nitrate nonahydrate, and aluminum hydroxide (gibbsite). The inorganic gel precursor can also be a partially hydrolyzed form of any of the aforementioned organometallic compounds or metal alkoxides, such as siloxanes and aluminoxanes.

The organic gel precursors include carbon and are polymerizable. In some cases, an organic gel precursor includes formaldehyde-resorcinol, formaldehyde plus other hydroxyl-substituted benzenes such as phenol and phloroglucinol, or other systems such as melamine-formaldehyde, urea-formaldehyde, and phenyldiamine-formaldehyde. In some cases, an organic gel precursor includes organic oligomers and/or macromers. In certain cases, the organic gel precursor is mixed with one or more additional organic compounds, such as sugar, furfuryl alcohol, or mesophase pitch.

In some implementations of process 100, the mixture of operation 102 is treated to form an inorganic wet gel in operation 104. The inorganic wet gel can be a gel formed, for example, by a sol-gel process. In some cases, a gel can be obtained by precipitation from a solution. Gels formed in operation 104 include an inorganic network component and a liquid including the organic gel precursors and the solvent. In some cases, the inorganic network component is an oxide, hydroxide, alkoxide, oxohydroxide, oxoalkoxide, oxo salt, or oxo salt hydrate of a metal, semi-metal, metalloid, or semi-conductor. In some cases, the inorganic network component is a hydrated form of a metal oxide. In some cases, the metal oxide includes main-group metal oxides, transition metal oxides, rare earth metal oxides, or any combination thereof. Exemplary oxides include alumina, tin oxide, antimony-doped tin oxide, titanium oxide, doped titanium oxide, zirconium oxide, yttria-stabilized zirconia, doped zirconium oxide, zinc oxide, doped zinc oxide, niobium oxide, and tantalum oxide. In some cases, the metal oxides can contain more than two different metal elements. In some cases, the metal oxides can be conducting or semi-conducting. In some cases, the metal oxide can be a transparent conducting oxide. Examples of transparent conducting oxides include tin oxide, indium tin oxide, doped tin oxides, antimony-doped tin oxide, fluorine-doped tin oxide, doped zinc oxides, aluminum-doped zinc oxide, $CuAlO_2$, $CuGaO_2$, and $AgGaO_2$.

In some cases, inorganic salt precursors are acidic in water, and the formation of a metal oxide gel takes place when the pH of the mixture increases due to the presence of an acid scavenger. Acid scavengers include epoxy-containing organic compounds such as ethylene oxide, propylene oxide, and epichlorohydrin; organic compounds such as urea that become basic upon hydrolysis; and inorganic bases such as ammonium hydroxide. For example, alumina gels from hydrates of aluminum chloride or nitrate as an inorganic salt precursor and propylene oxide as an acid scavenger are described by Baumann et al. in "Synthesis of High-surface-Area Alumina Aerogels without the Use of Alkoxide Precursors," *Chemistry of Materials* 2005, 17, 395-401, which is incorporated by reference herein.

Gels formed in operation 104 are then treated to form an organic polymer gel network in the body of the gel in operation 106. In some cases, the organic polymers can be pyrolytic. In certain cases, the organic polymer gel precursors are organic oligomers and/or macromers. Treating the gel in operation 106 may be conducted at a temperature higher than the temperature in operation 104. In some cases, the organic polymer gel precursor may partially undergo polymerization in operation 104. Treating the gel in operation 106 may promote the polymerization for more complete formation of the organic polymer gel network.

In certain cases, gels formed in operation 104 can catalyze the organic polymerization in operation 106. Without binding to any theory, some metal oxide gels have M-OH hydroxyl groups on the surface which are Brönsted acid sites and can promote polymerization.

Gels treated in operation 106 are then treated in operation 108 to remove the liquid component from the wet gel and to form a porous composite material. The liquid is removed to provide a porous inorganic-organic composite material. The liquid component in the composite gel can be removed by a process such as drying, supercritical drying, cryogenic drying, heating, or the like. The drying yields a composite xerogel which can have a porosity lower than expected from supercritical drying or cryogenic drying. In some implementations, the heating can cause dehydration, decomposition, combustion, or pyrolysis of a part of the solid component.

Optional operation 110 includes processing the product of operation 108 to remove the inorganic network component or the organic network component to produce a porous material. In an example, the product from operation 108 is a porous alumina-resorcinol/formaldehyde polymer composite that is further heated in operation 110 to burn off the polymer component. This leaves calcined and dehydrated alumina that is porous. Other examples of porous materials from operation 110 include metal oxides such as tin oxide, antimony-doped tin oxide, titanium oxide, doped titanium oxide, zirconium oxide, yttria-stabilized zirconia, doped zirconium oxide, zinc oxide, doped zinc oxide, niobium oxide, and tantalum oxide. In some cases, the metal oxides can contain more than two different metal elements. In some cases, the metal oxides can be conducting or semi-conducting. In some cases, the metal oxides can be a transparent conducting oxide. Examples of transparent conducting oxides include tin oxide, indium tin oxide, doped tin oxides, antimony-doped tin oxide, fluorine-doped tin oxide, doped zinc oxides, aluminum-doped zinc oxide, $CuAlO_2$, $CuGaO_2$, and $AgGaO_2$. In some cases, the porous materials from operation 110 can have a heterogeneous structure including more than one metal oxide or a plurality of metal oxides. One example of a heterogeneous structure is a porous network structure embedded with metal oxide nanoparticles inside. In some cases, the heating in operation 110 results in decomposition of a metal oxide. One example of the metal oxides is $Au_2O$. In some cases, the porous materials from operation 110 have a porous metal oxide structure embedded with metal nanoparticles inside. Alternatively, the product of operation 108 can be soaked in an etching solution to etch out the inorganic network component to yield a porous polymer material.

Optional operation 112 includes processing the product of operation 108 to pyrolyze the polymer component with a limited amount of oxygen to form a porous metal oxide-carbon composite material. Examples of the metal oxide include alumina, tin oxide, antimony-doped tin oxide, titanium oxide, doped titanium oxide, zirconium oxide, yttria-stabilized zirconia, doped zirconium oxide, zinc oxide, doped zinc oxide, niobium oxide, and tantalum oxide. In some cases, the metal oxides can contain more than two different metal elements. In some cases, the metal oxides can be conducting or semi-conducting. In some cases, the metal oxides can be transparent conducting oxides. Examples of transparent conducting oxides include tin oxide, indium tin oxide, doped tin oxides, antimony-doped tin oxide, fluorine-doped tin oxide, doped zinc oxides, aluminum-doped zinc oxide, $CuAlO_2$, $CuGaO_2$, and $AgGaO_2$. Pyrolysis with a limited amount of oxygen may result in partial or incomplete pyrolysis to yield a composite material with discontinuous carbon networks, isolated carbonaceous areas, or a combination thereof in a metal oxide network. In some cases, during the pyrolysis in operation 112 the metal oxide component undergoes a carbothermal reaction with a sufficient amount of carbon and hence results in porous carbon embedded with metal particles inside. One example is the formation of porous carbon embedded with Sn metal particles inside.

In some cases, the pyrolysis in operation 112 with a limited amount of oxygen results in decomposition of a metal oxide. One example of the metal oxides is $Au_2O$. In some cases, the pyrolysis in operation 112 with a limited amount of oxygen results in a carbothermal reaction of a metal oxide. One example of carbothermal reaction is the formation of iron metal upon the reaction between iron oxides and the carbon at high temperatures. In some cases, the pyrolysis in operation 112 with a limited amount of oxygen produces a porous metal oxide structure embedded with discrete carbon and metal nanoparticles inside.

Optional operation 114 includes processing the product of operation 112 to remove one of the network components (e.g., metal oxide or carbon). In one example, a porous alumina-carbon composite can be heated with an excess of oxygen to burn off the carbon and thus to produce a porous alumina. In another example, the porous alumina-carbon composite can be soaked in sulfuric acid and heat-treated in a pressurized container to etch out the alumina component and form porous carbon.

Figure 1B:
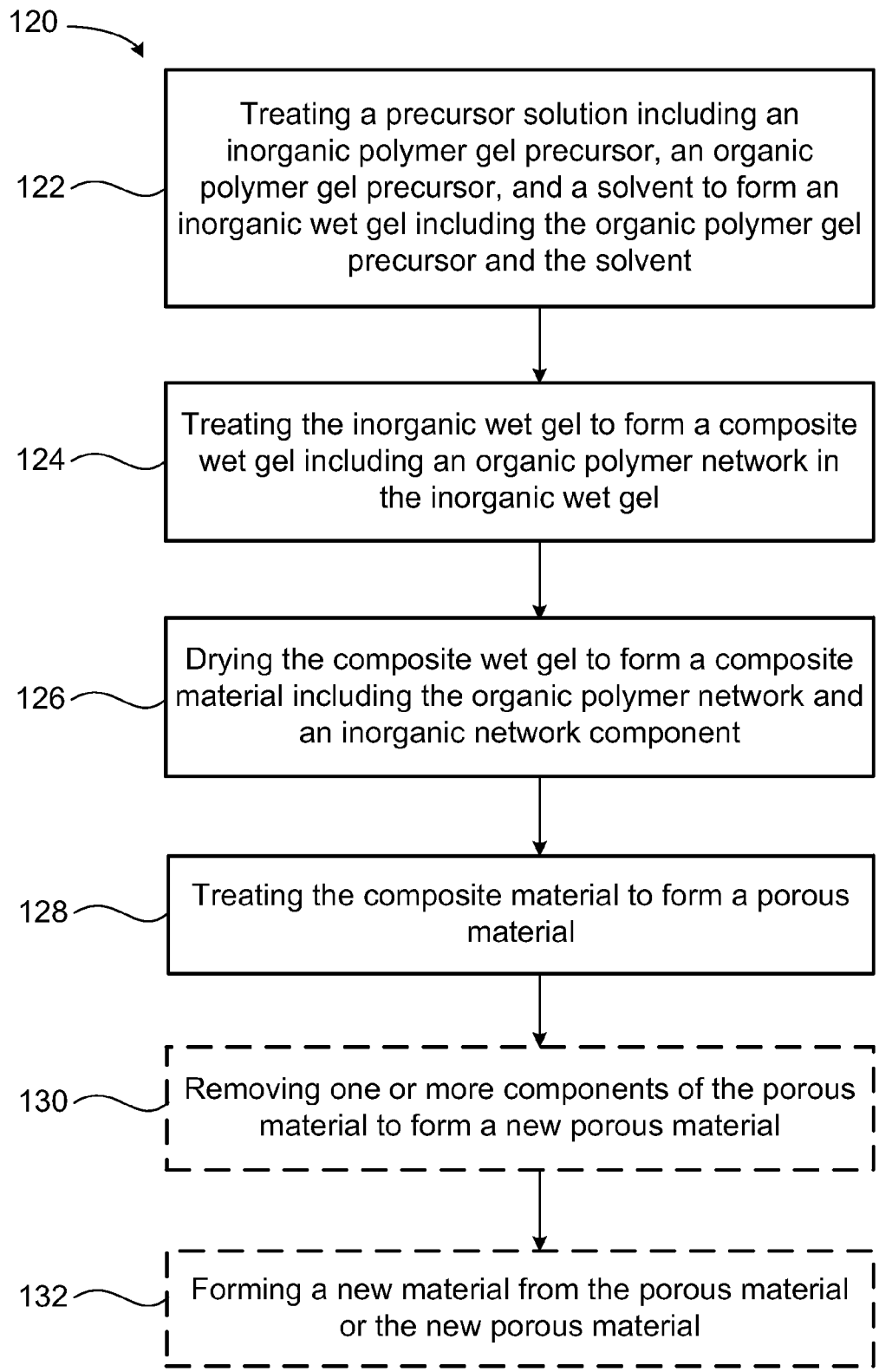

In process 120, shown in FIG. 1B, a solution including an inorganic polymer gel precursor, an organic polymer gel precursor, and a solvent is treated in operation 122 to form an inorganic wet gel including the organic polymer gel precursor and the solvent. The inorganic wet gel is treated in operation 124 to form a composite wet gel including an organic polymer network throughout the inorganic wet gel. In operation 126, the composite wet gel is dried to form a composite material including the organic polymer network and an inorganic network component. The composite material may be a porous composite material. The composite material can be further treated in operation 128 to remove at least one component from the composite material to form a porous (or another porous) material. In optional operation 130, one or more additional components of the porous material may be removed to yield a new porous material. In optional operation 132, the porous material formed in operation 128 or 130 may be used as a reactant or component to form a new material.

In some cases, process 120 can be applied more than once on the same material to form a heterogeneous composite structure. Examples of the heterogeneous composite structures include a core/shell structure and a multi-layer structure.

The porous materials, composites, and materials described herein can be used in a variety of ways including, but not limited to, adsorbents, absorbents, nanoreactors, nanoglues, nanocontainers, nanocomposites, nanoelectrodes, catalysts, catalyst supports, oxidizing agents, reducing agents, filters, chromatography media, ion exchange materials, separation materials, magnetic separation materials, membranes, gas/liquid/fuel storage materials, electrodes, sensors, electrical materials, electronic materials, magnetic materials, microwave absorbers, microwave-assisted heating materials, bio-implants, structure reinforcing materials, construction materials, solar energy collectors, supercapacitors, pseudocapacitors, solar cell components, dielectrics, thermal insulation materials, sound insulation materials, fire retardants, paint thickeners, matting agents, packaging materials, refractories, additives, ink jet coatings, porous binders, porous fillers, ionic conductors, bioreactors, culture media, culture supports, bone replacement materials, active battery components, battery separators, thermal composites (e.g., porous materials impregnated with a thermal energy storage material, a phase change compound, a thermochemical energy storage material, or a magnetocaloric material), toxin removal materials, chemical removal materials, waste removal materials, hazard removal materials, chemical decontaminants, bioactive decontaminants, odor elimination materials, oil spill cleanup materials, arsenic removal materials, heavy metal removal materials, nuclear waste removal materials, energetic materials, evaporative chillers/heaters, aroma delivery materials, flavor delivery materials, drug delivery materials, sanitizer delivery materials, herbicide delivery materials, fungicide delivery materials, pesticide delivery materials, insecticide delivery materials, plant nutrient delivery materials, fertilizer materials, plant growing media, green roof materials, hydroponics support media, potting materials, animal nutrient delivery materials, human nutrient delivery materials, water purification materials, water desalination materials, capacitive deionization electrodes, soil stabilization materials, wetting agents, water absorption materials, water adsorption materials, water collection materials, water retention materials, humidity control materials, pet litter absorption materials, vapor sorption materials, gas sorption materials, oil sorption materials, oil extraction materials, algae oil nanofarming materials, selective solid-phase extraction materials, desiccants, proppant materials, hemostats, and the like. The porous materials and composites described herein can also be used as a template or a mask to produce other porous materials, including porous polymers and porous ceramics.

The following examples are provided for illustration. It should be appreciated by those of skill in the art that the techniques disclosed in the following examples are considered to be exemplary. However, those of skill in the art should, in light of the present disclosure, appreciate that many changes can be made in the specific embodiments that are disclosed without departing from the spirit and scope of this disclosure.

EXAMPLES

Alumina

Figure 2:
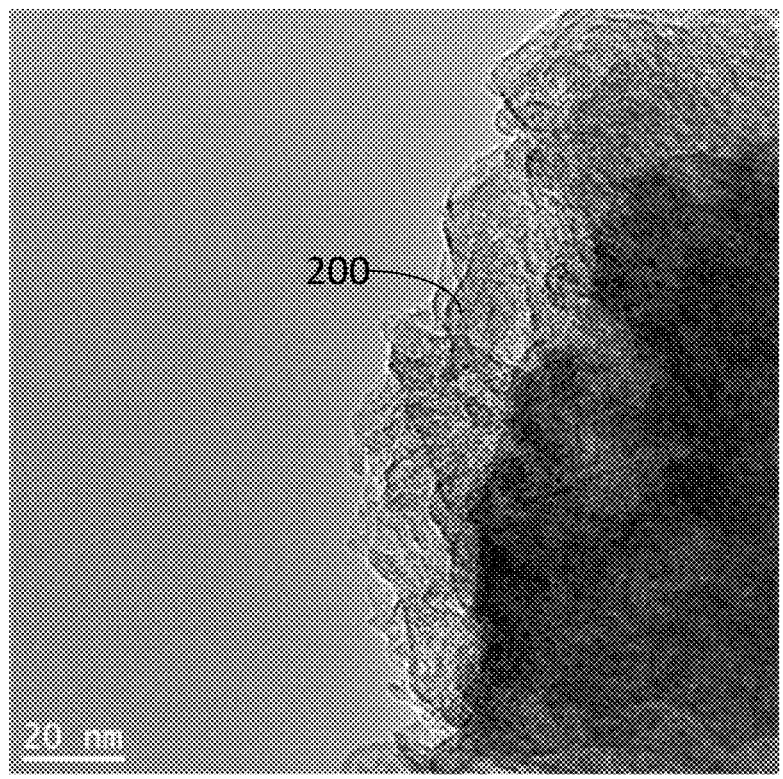
FIG. 2 is a transmission electron micrograph of porous alumina-resorcinol/formaldehyde composite xerogel (sample 1a) formed by the method described in Example 1.
Figure 7:
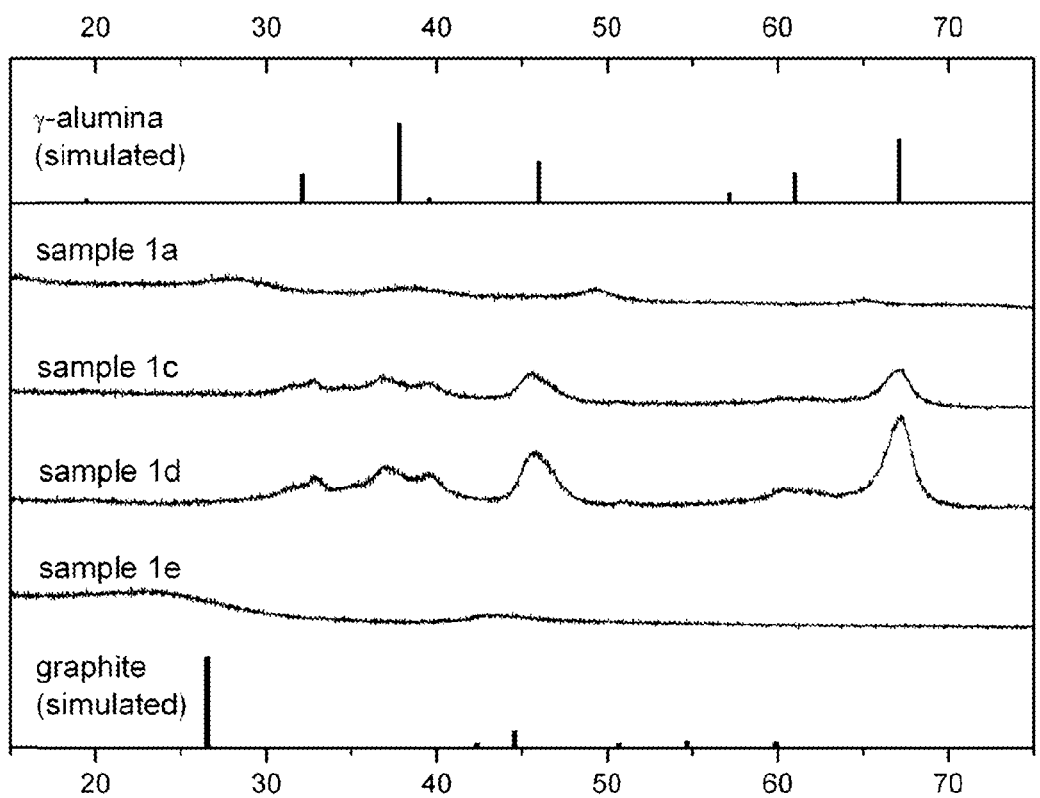
FIG. 7 shows powder X-ray diffraction patterns of samples 1a, 1c, 1d, and 1e by the method described in Example 1.
Figure 8:
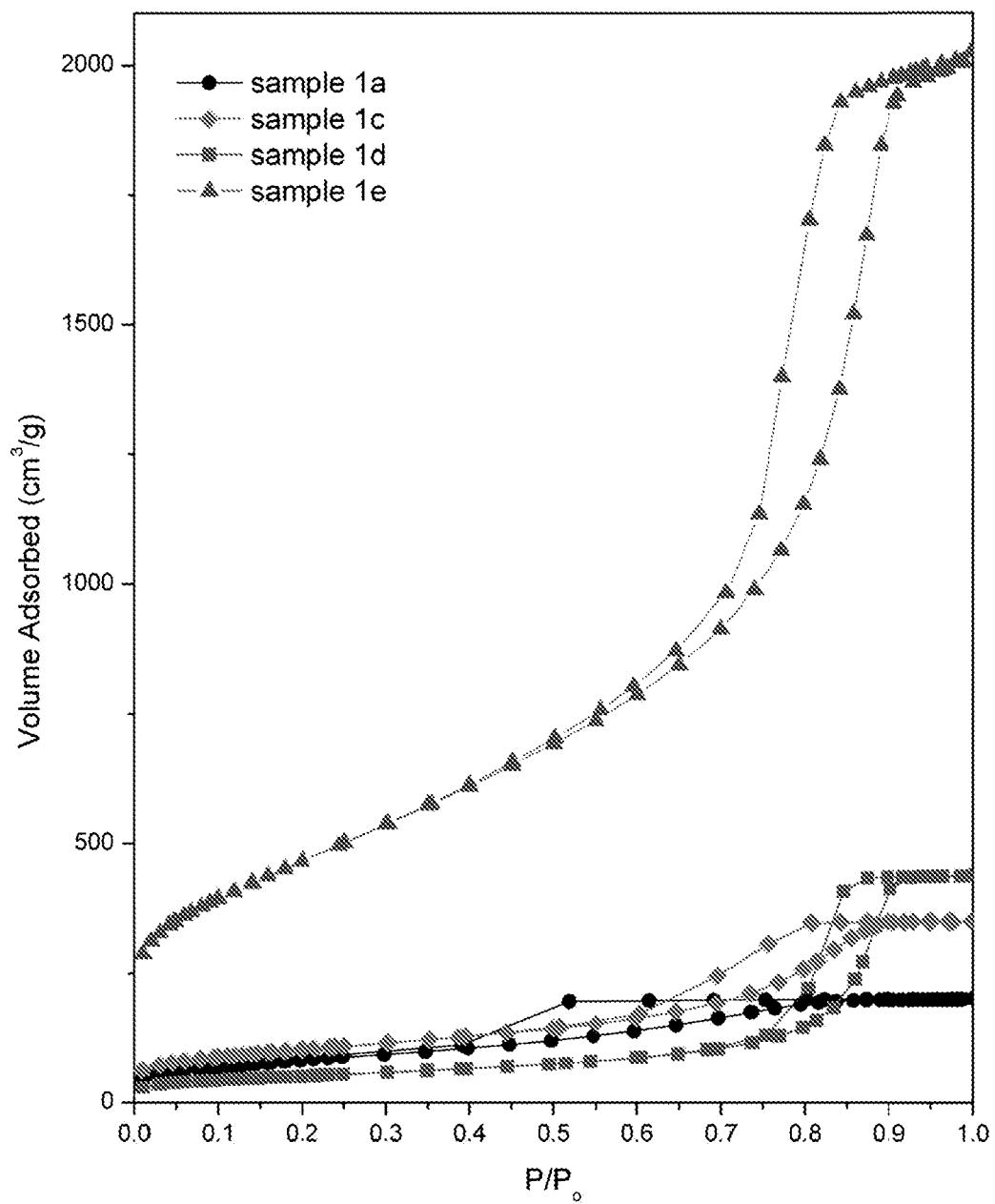
FIG. 8 shows $N_2$ sorption isotherms of samples 1a (circle), 1c (diamond), 1d (square), and 1e (triangle).
Figure 9:
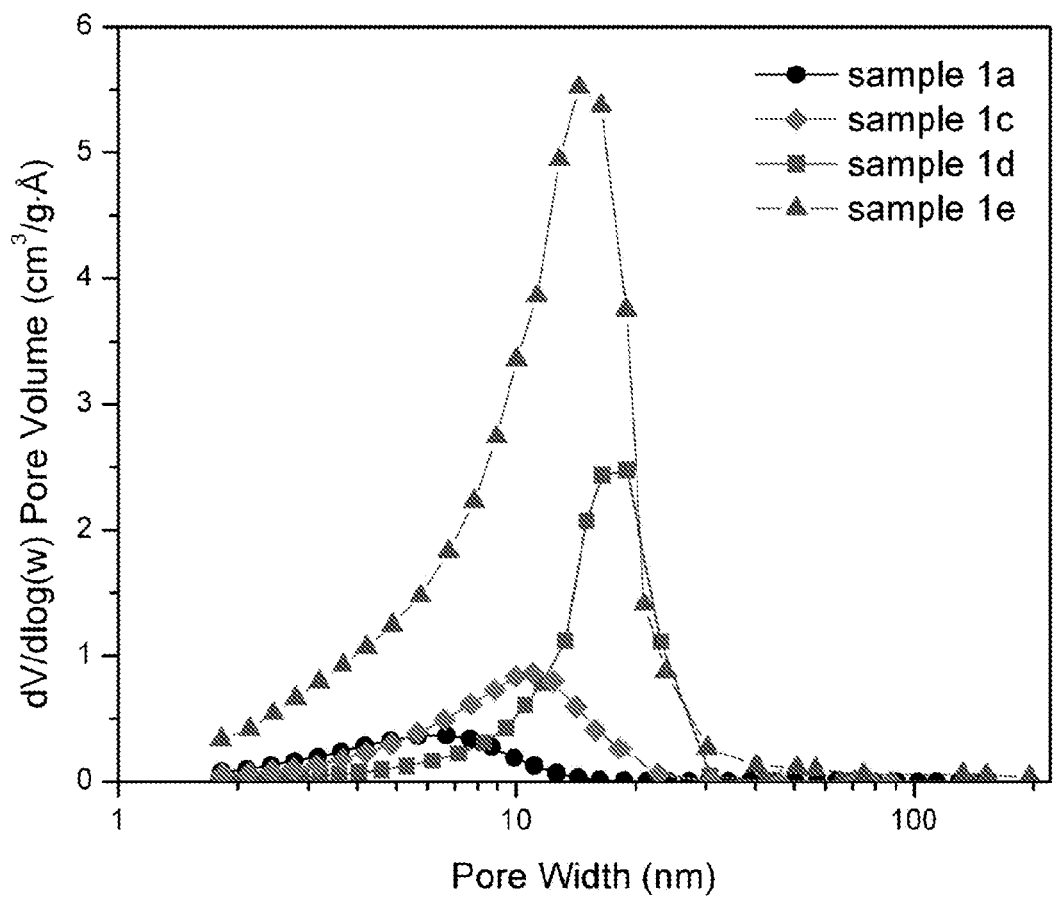
FIG. 9 shows BJH pore size distributions of samples 1a (circle), 1c (diamond), 1d (square), and 1e (triangle).

A precursor solution was prepared by dissolving 7.1 g $AlCl_3 \cdot 6H_2O$ and 1.0 g of resorcinol in 61 ml of a 50/50 v/v mixture of water and ethanol. To this solution 1.48 g 37% formaldehyde solution was added and stirred to form a solution of pH 2 to 3. 17.1 g of propylene oxide was added to this precursor solution and mixed thoroughly. The alumina component gelled within about 90 minutes at room temperature into a transparent colorless gel of pH 5 to 6. The lack of color indicated that resorcinol and formaldehyde did not polymerize in any appreciable amount during this time. This gel was placed in an oven at 70° C. for about 18 hours. After the heating, the gel became hard, red-colored, and yet transparent, with a few milliliters of clear colorless liquid on top. To prepare the xerogel (sample 1a), the gel was chopped into pieces less than 1 $cm^3$ in size and left in air to dry for about 20 hours. A transmission electron micrograph of the product 200 is shown in FIG. 2. The powder X-ray diffraction pattern (sample 1a in FIG. 7) shows very broad Bragg peaks that correspond to gelatinous hydrous aluminum oxide or pseudo-boehmite, AlO(OH). The $N_2$ sorption isotherms and BJH pore distribution are shown in FIG. 8 and FIG. 9, respectively. The product exhibited a BET specific surface area of 300 $m^2/g$, a total pore volume of 0.31 $cm^3/g$, and an average pore size of 4.1 nm.

Figure 3:
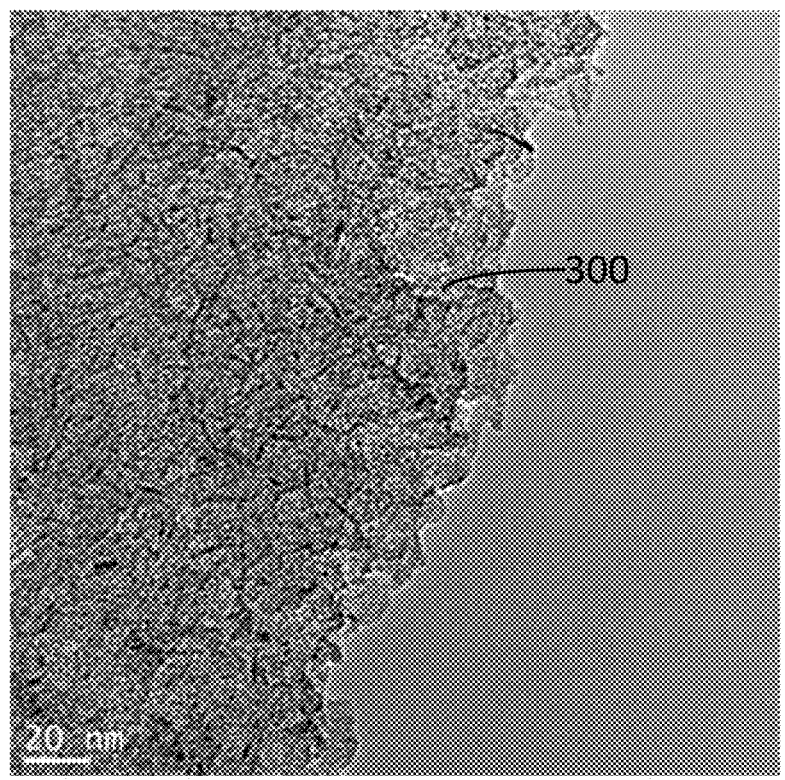
FIG. 3 is a transmission electron micrograph of porous resorcinol/formaldehyde polymer material (sample 1b) formed by the method described in Example 1.

To prepare porous resorcinol/formaldehyde polymer material (sample 1b), the composite xerogel was then soaked in dilute HCl solution overnight so as to etch out the alumina. The product was then taken out, rinsed repeatedly with deionized water, and dried in a lab oven at about 110° C. overnight. The shape and size of the final product were not noticeably different from the original composite xerogel. The product was amorphous based on the powder X-ray diffraction studies (not shown). Although the nanopores can be found in the transmission electron micrograph of the product 300 shown in FIG. 3, the $N_2$ sorption analysis results did not allow a meaningful interpretation in regard to its porosity (not shown).

Figure 4:
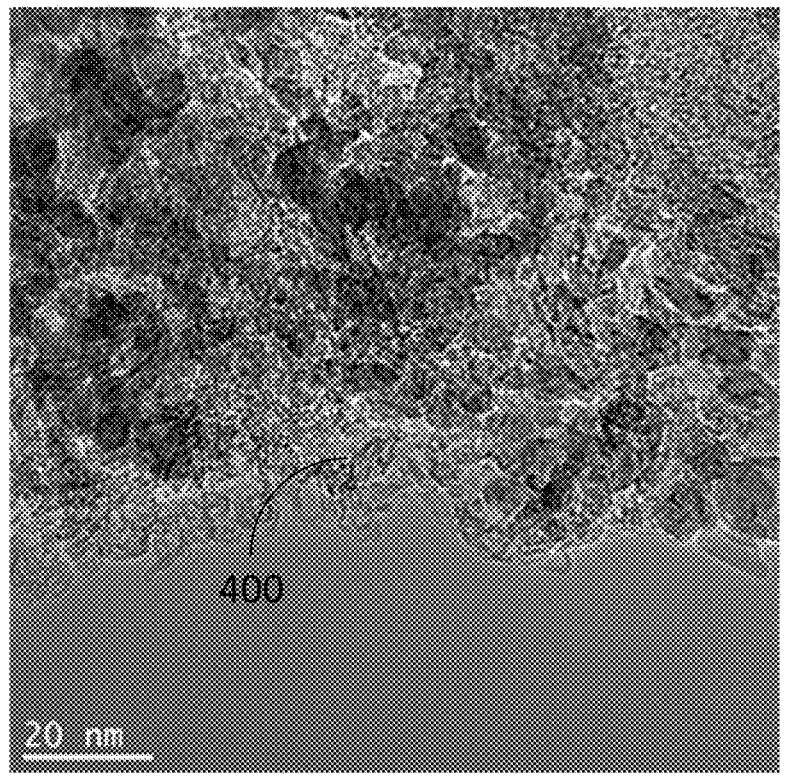
FIG. 4 is a transmission electron micrograph of porous alumina-carbon composite (sample 1c) formed by the method described in Example 1.

To prepare the aluminum oxide-carbon composite (sample 1c), some of the xerogel was placed in a tube furnace purged with Ar gas and heated to 1000° C. at a rate of 6°/min and held for 3 hours under flowing Ar. The product was black and kept the original shape and size upon visual inspection. A transmission electron micrograph of the product 400 is shown in FIG. 4. The powder X-ray diffraction pattern (sample 1c in FIG. 7) shows broad Bragg peaks that correspond to γ-alumina. The $N_2$ sorption isotherms and BJH pore distribution are shown in FIG. 8 and FIG. 9, respectively. The product exhibited a BET specific surface area of 367 $m^2/g$, a total pore volume of 0.54 $cm^3/g$ and an average pore size of 5.9 nm.

Figure 5:
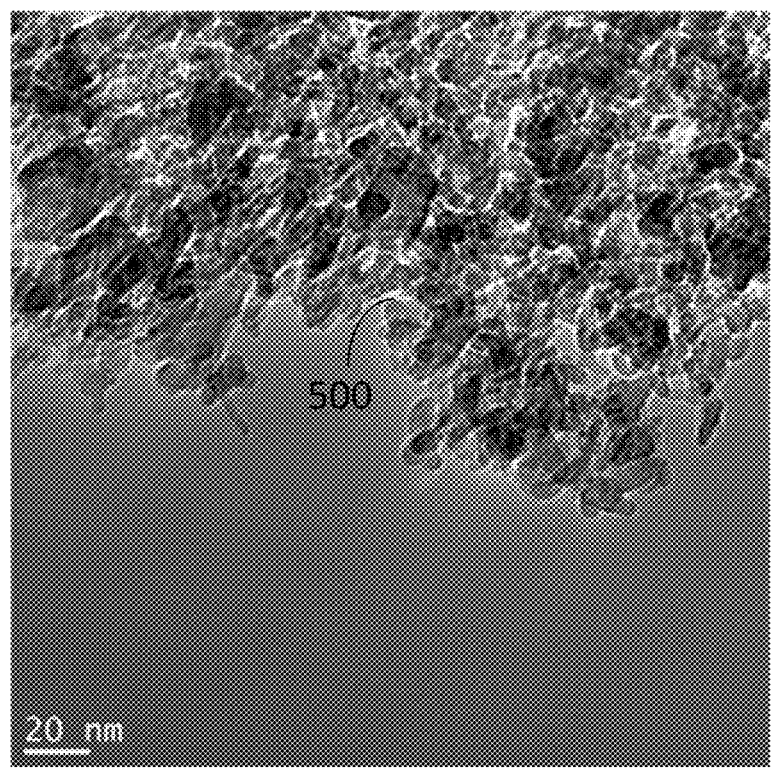
FIG. 5 is a transmission electron micrograph of porous alumina (sample 1d) formed by the method described in Example 1.

To prepare porous aluminum oxide (sample 1d), some of the aluminum oxide-carbon composite material was placed in a box furnace and heated in air to 700° C. at a rate of 100° C./hour, held for 10 hours, and cooled radiatively to room temperature. The product was semi-transparent and kept the original shape and size upon visual inspection. A transmission electron micrograph of the product 500 is shown in FIG. 5. The product was γ-alumina according to its powder X-ray diffraction pattern (sample 1d in FIG. 7) and exhibited a BET specific surface area of 183 $m^2/g$, a total pore volume of 0.68 $cm^3/g$, and an average pore size of 14.8 nm. The $N_2$ sorption isotherms and BJH pore distribution are shown in FIG. 8 and FIG. 9, respectively.

Figure 6:
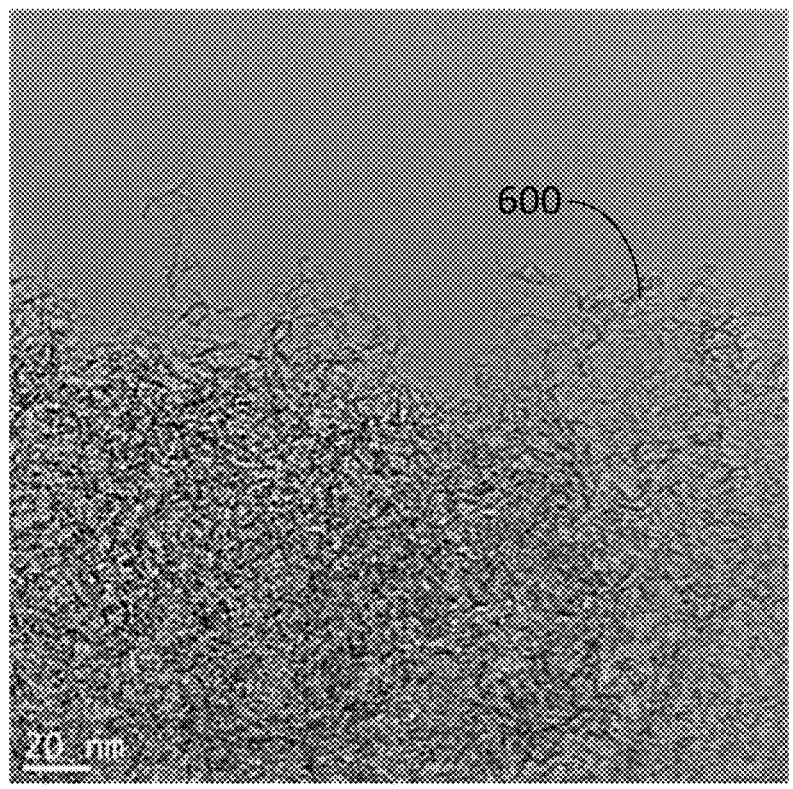
FIG. 6 is a transmission electron micrograph of porous carbon (sample 1e) formed by the method described in Example 1.

To prepare porous carbon (sample 1e), some of the aluminum oxide-carbon composite was placed in a Parr acid digestion bomb with 9 g of ~32% $H_2SO_4$, sealed, and heated at 160° C. for about 20 hours. The product was then washed with 32% $H_2SO_4$ and copious amounts of water until the wash water was pH neutral. The product was then taken out and dried in a lab oven at about 110° C. overnight. The dried product was light-weight and kept the original color, shape, and size upon visual inspection. A transmission electron micrograph of the product 600 is shown in FIG. 6. The powder X-ray diffraction pattern (sample 1e in FIG. 7) shows very broad Bragg peaks that correspond to graphite. The $N_2$ sorption isotherms and BJH pore distribution are shown in FIG. 8 and FIG. 9, respectively. The product exhibited a BET specific surface area of 1678 m²/g, a total pore volume of 3.11 cm³/g, and an average pore size of 7.4 nm.

Figure 10:
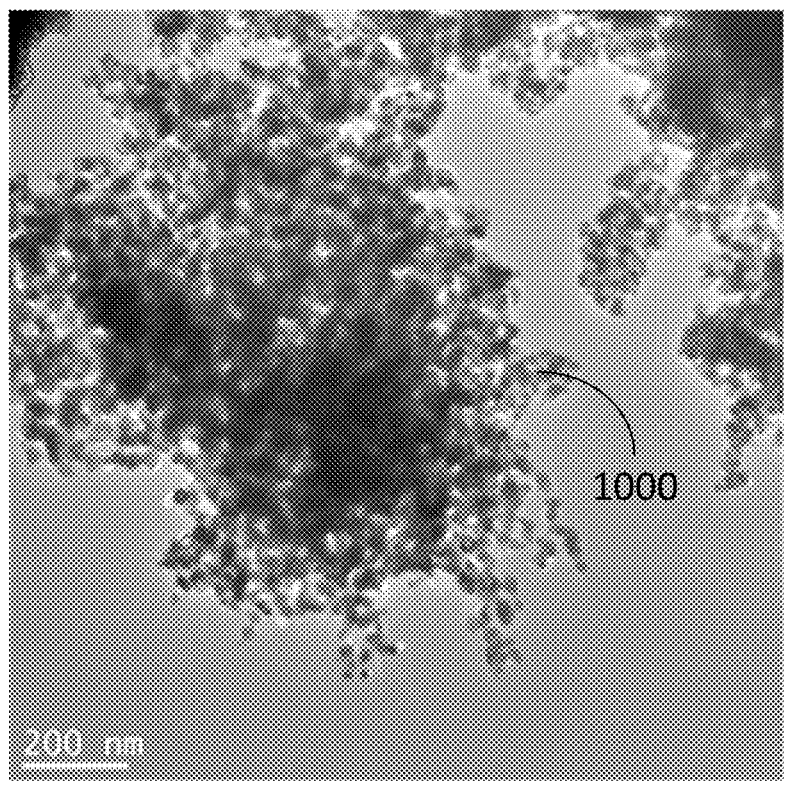
FIG. 10 is a transmission electron micrograph of porous tin oxide (sample 2) formed by the method described in Example 2.
Figure 11:
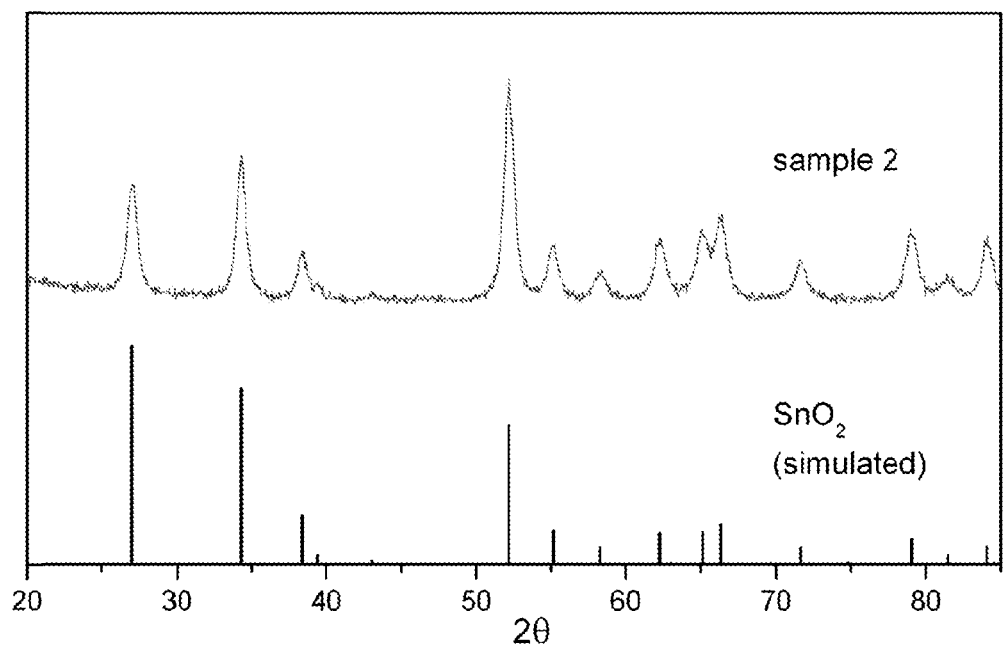
FIG. 11 is a powder X-ray diffraction pattern of porous tin oxide (sample 2) formed by the method described in Example 2.
Figure 12:
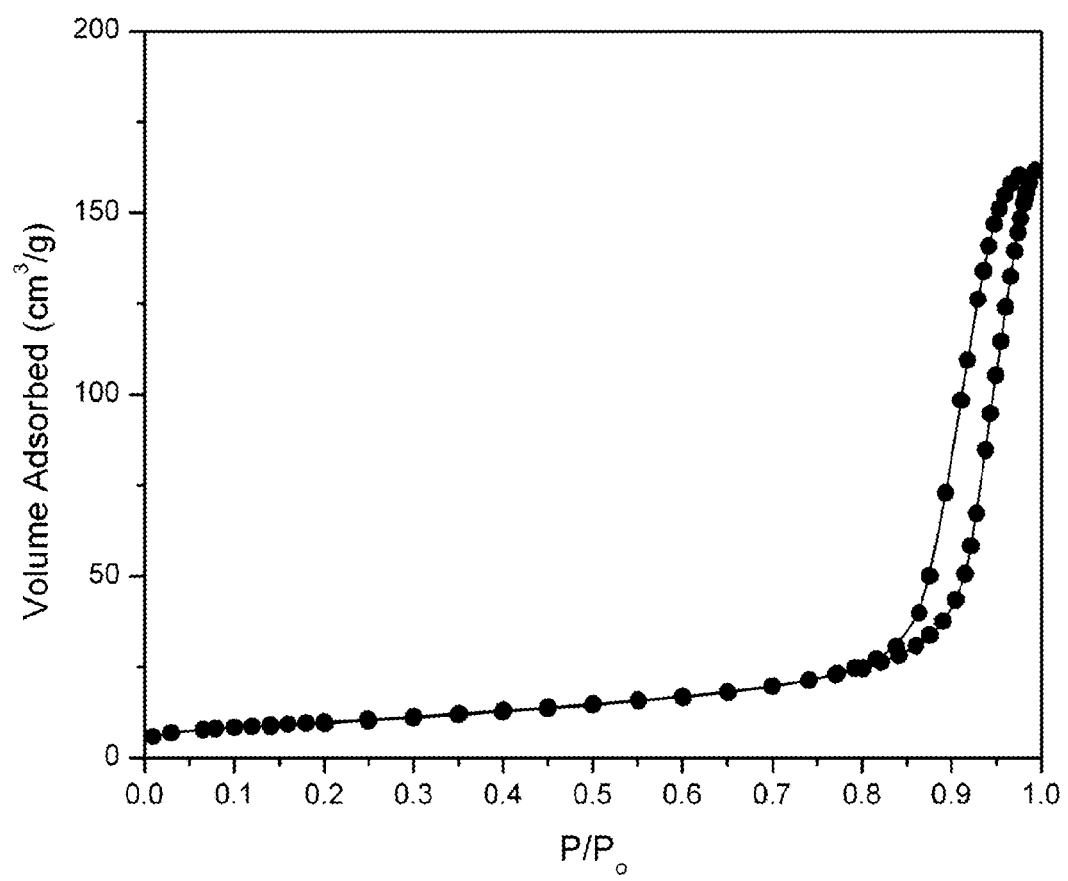
FIG. 12 shows a $N_2$ sorption isotherm of porous tin oxide (sample 2) formed by the method described in Example 2.
Figure 13:
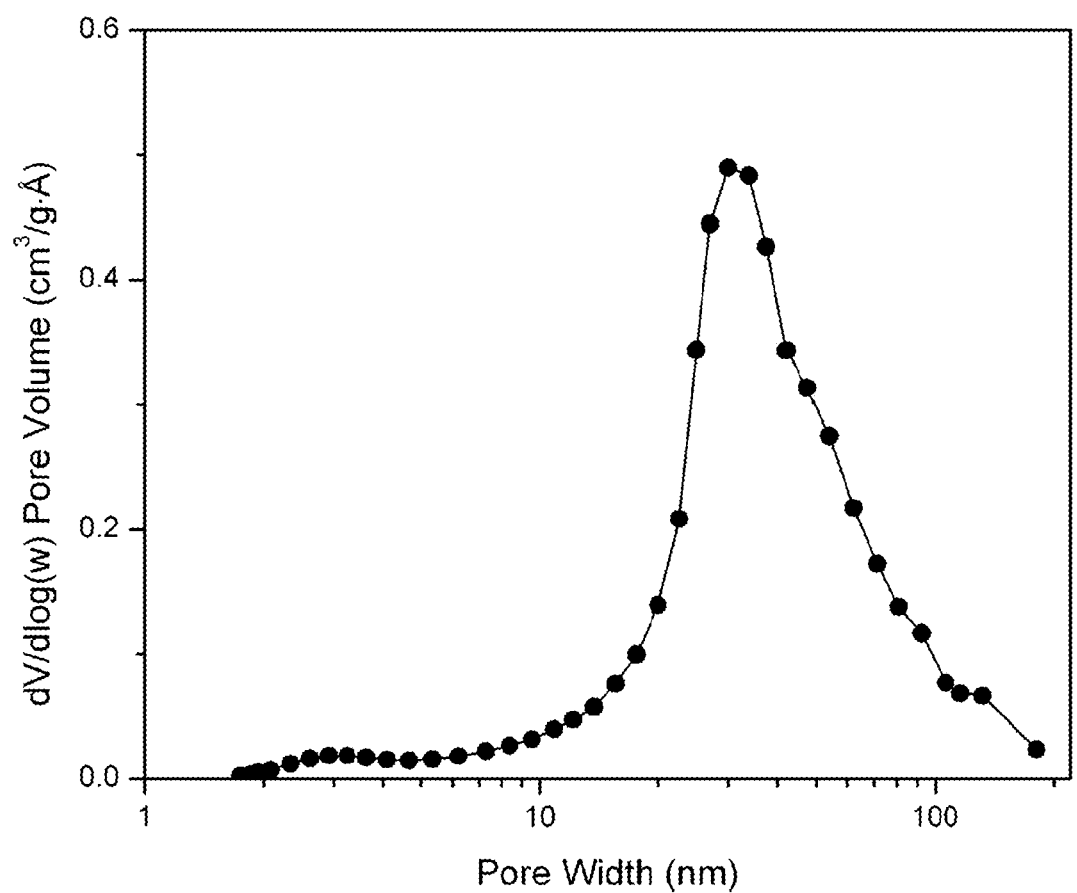
FIG. 13 shows a BJH pore size distribution of porous tin oxide (sample 2) formed by the method described in Example 2.
Figure 20:
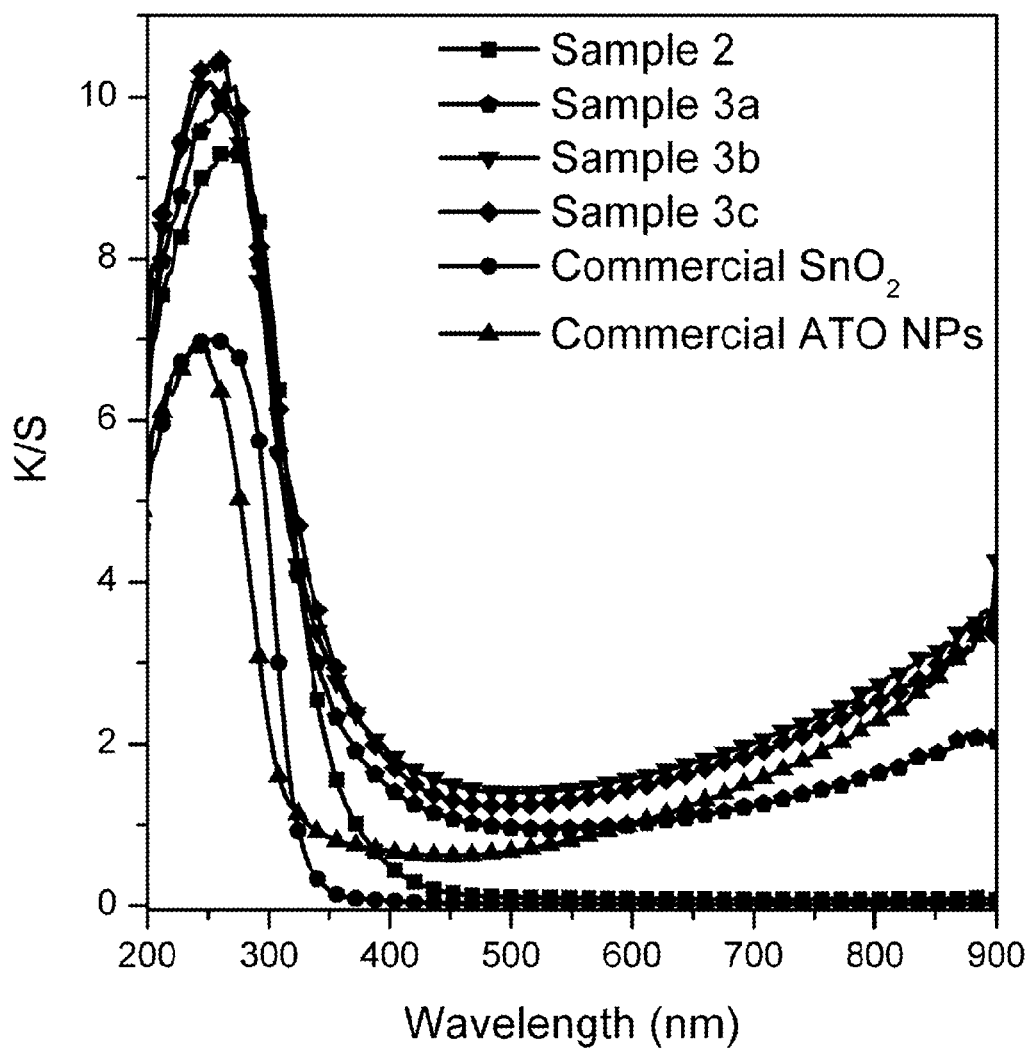
FIG. 20 shows Kubelka-Munk transforms of UV-VIS diffuse reflectance spectra of samples 2 (square), 3a (pentagon), 3b (inverse triangle) and 3c (diamond), together with two reference samples, commercial $SnO_2$ particles (circle; Alfa Aesar, 99.9%, <10 µm) and a commercial antimony-doped tin oxide (ATO) nanoparticles (triangle; Sigma Aldrich, 7-11 at % Sb, 99.5%, <50 nm, specific surface area ~47 $m^2/g$).

Tin Oxide 2.8 g SnCl$_4$.5H$_2$O, 1.0 g of resorcinol, and 1.57 g 37% formaldehyde solution were dissolved in 13 ml of a 50/50 v/v mixture of water and ethanol to produce the precursor solution at a pH of about 2. This mixture was placed in an ice-water bath with stirring for 10 minutes. 4.0 g of propylene oxide was added with stirring to the mixture while on the ice bath. The solution was stirred for about 90 seconds then removed from the ice bath. After this, the mixture gelled in about 1 minute. The gel was light yellow in color, which is associated with tin oxide gels prepared without organic polymer gel precursors. Lack of significant colorization in the gel indicated that resorcinol and formaldehyde did not polymerize in an appreciable amount during this time. After sitting for one day, the gel shrank about 15% to provide a dark yellow gel with clear colorless liquid around the gel. The gel was placed in an oven at 76° C. for 5 days, after which the tin oxide gel was a hard orange gel surrounded by soft, opaque, light orange polymer. After air drying for 3 days, the xerogels were burned in an electric heater for 1 to 2 minutes, then heated in a box furnace for 10 hours at 500° C. to produce a light off-white product with measurable conductance. The products kept the original shape and size upon visual inspection. A transmission electron micrograph of the product 1000 is shown in FIG. 10. The powder X-ray diffraction pattern of the product (FIG. 11) shows Bragg peaks that are assigned to tin oxide. The N$_2$ sorption isotherms and BJH pore distribution are shown in FIG. 12 and FIG. 13, respectively. The BET specific surface area was 35.7 m²/g with a pore volume of 0.25 cm³/g and a BJH average pore size of 27.8 nm. The UV-VIS diffuse reflectance spectrum for sample 2 is given in FIG. 20 together with some other samples after a Kubelka-Munk transformation was applied to the diffuse reflectance data to provide a better interpretation of the weakly absorbing samples.

Figure 14:
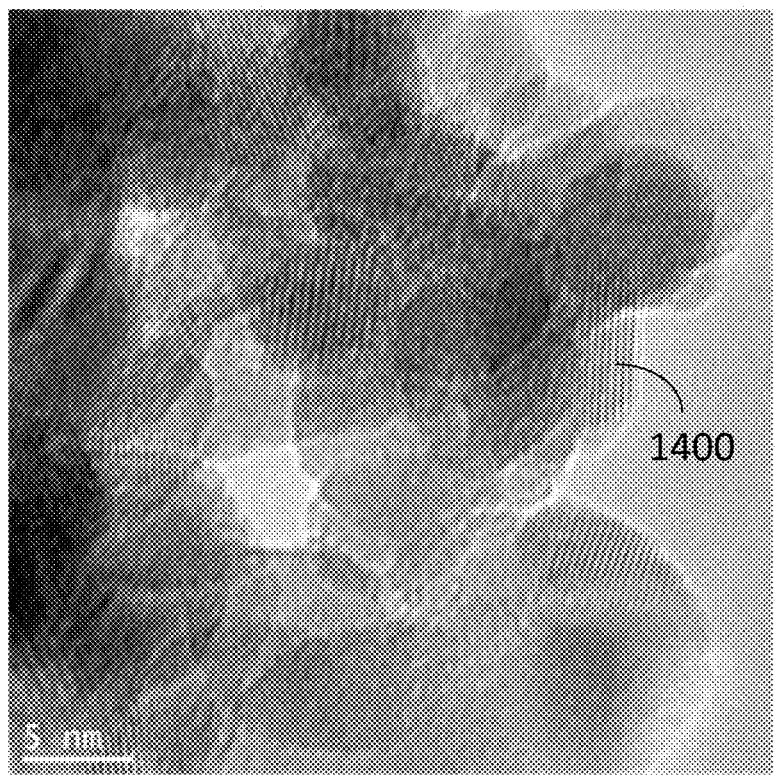
Figure 17:
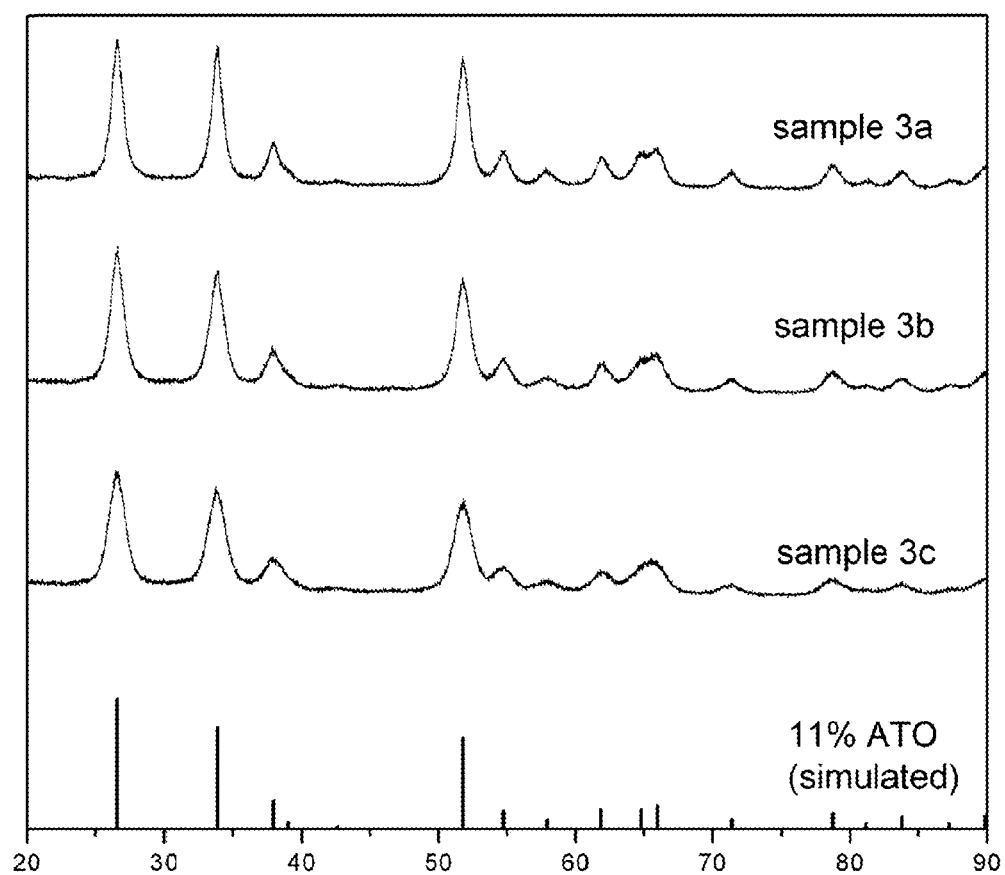
FIG. 17 shows powder X-ray diffraction patterns of samples 3a-3c formed by the method described in Examples 3a-3c.
Figure 18:
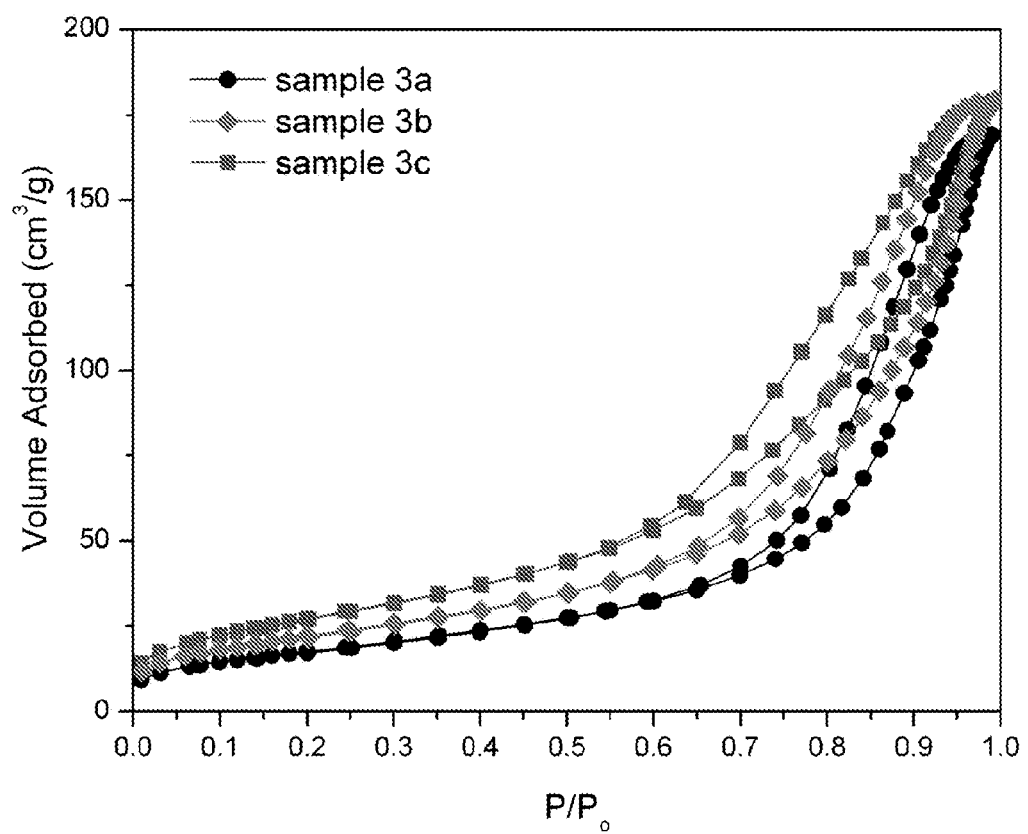
FIG. 18 shows $N_2$ sorption isotherms of porous antimony-doped tin oxides formed by the method described in Example 3a (sample 3a, circle), Example 3b (sample 3b, diamond), and Example 3c (sample 3c, square).
Figure 19:
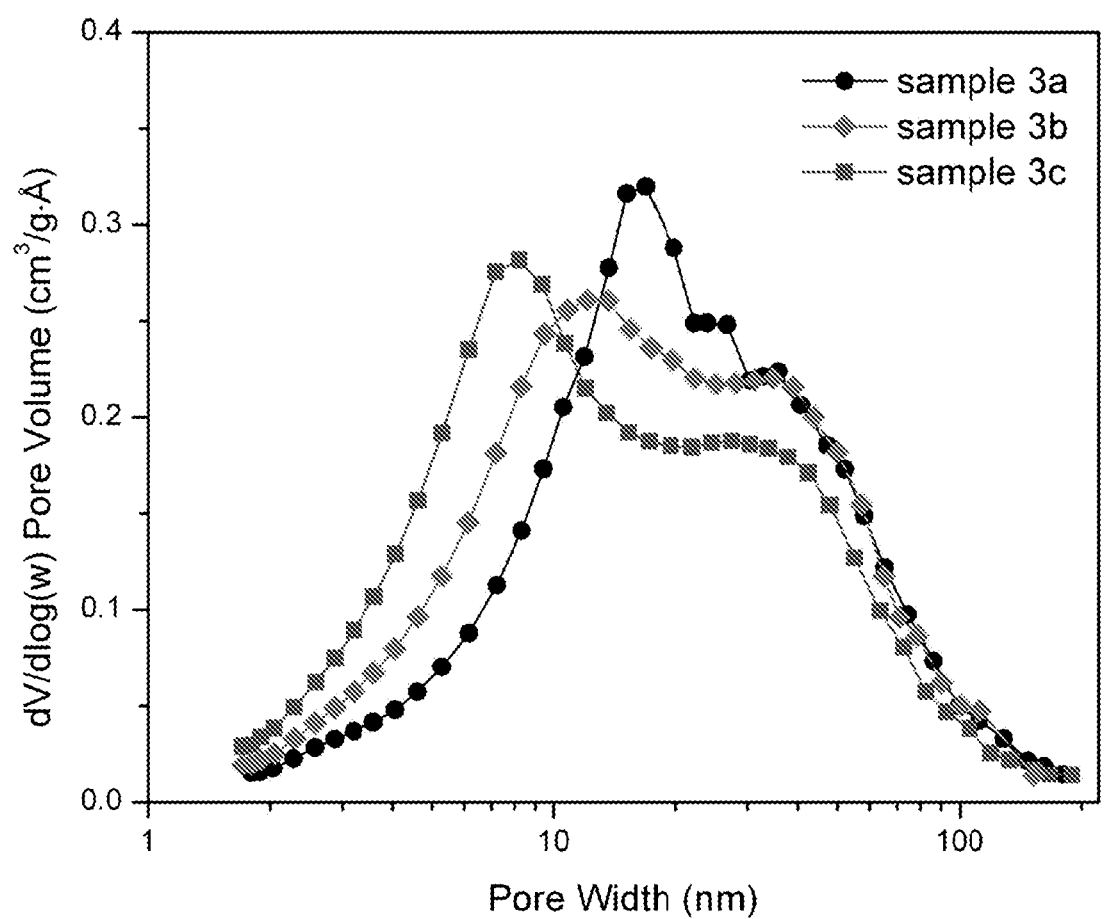
FIG. 19 is a BJH pore size distribution of porous antimony-doped tin oxides formed by the method described in Example 3a (sample 3a, circle), Example 3b (sample 3b, diamond), and Example 3c (sample 3c, square).

Antimony-Doped Tin Oxide 2.8 g SnCl$_4$.5H$_2$O, 0.057 g SbCl$_3$, 1.0 g of resorcinol, and 1.48 g 37% formaldehyde solution were dissolved in 14 ml of a 50/50 v/v mixture of water and ethanol to produce the precursor solution at a pH of about 2. This mixture was placed in an ice-water bath with stirring for 10 minutes. 4.0 g of propylene oxide was added with stirring to the mixture while on the ice bath. The solution was stirred for about 90 seconds then removed from the ice bath. After this, the mixture gelled in about 1 minute. The gel was light yellow in color, which is associated with antimony/tin oxide gels prepared without organic polymer gel precursors. Lack of significant colorization in the gel indicated that resorcinol and formaldehyde did not polymerize in an appreciable amount during this time. After sitting for one day, the gel shrank about 20% to provide an opaque red/orange gel with transparent yellow liquid around the gel. The gel was placed in an oven at 70° C. for 5 days after which the antimony-doped tin oxide gel was a hard opaque red/brown gel surrounded by clear, light yellow liquid. After air drying for several days, the dried gels were burned in an electric heater for 1 to 2 minutes then heated in a box furnace in air for 10 hours at 500° C. to produce a low-density, dark blue product with measurable conductance. The product kept the original shape and size upon visual inspection. A transmission electron micrograph of the product 1400 is shown in FIG. 14. The powder X-ray diffraction pattern of the product (sample 3a in FIG. 17) shows Bragg peaks that are assigned to antimony-doped tin oxide. The N$_2$ sorption isotherms and BJH pore distribution are shown in FIG. 18 and FIG. 19, respectively. The BET specific surface area was 65 m²/g with a pore volume of 0.26 cm³/g and an average pore size of 16.1 nm (4V/A by BET) (sample 3a). The UV-VIS diffuse reflectance spectrum for sample 3a is given in FIG. 20 together with some other samples after a Kubelka-Munk transformation was applied.

Figure 15:
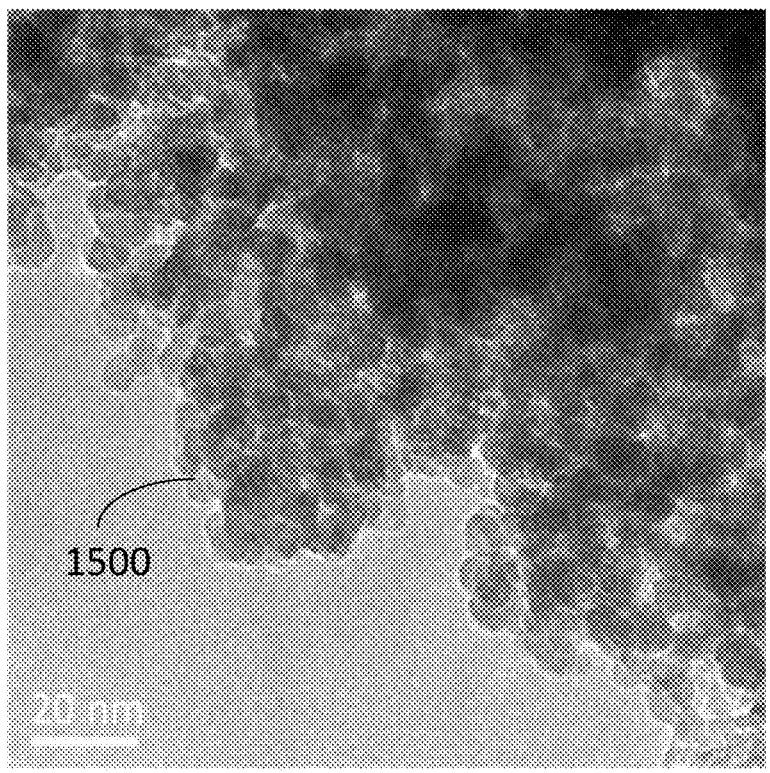
FIG. 15 is a transmission electron micrograph of porous antimony-doped tin oxide (sample 3b) formed by the method described in Example 3b.

Antimony-Doped Tin Oxide 2.8 g SnCl$_4$.5H$_2$O, 0.11 g SbCl$_3$, 1.0 g of resorcinol, and 1.48 g 37% formaldehyde solution were dissolved in 14 ml of a 50/50 v/v mixture of water and ethanol to produce the precursor solution at a pH of about 2. This mixture was placed in an ice-water bath with stirring for 10 minutes. 4.0 g of propylene oxide was added with stirring to the mixture while on the ice bath. The solution was stirred for about 90 seconds then removed from the ice bath. After this, the mixture gelled in about 1 minute. The gel was light yellow in color, which is associated with antimony/tin oxide gels prepared without organic polymer gel precursors. Lack of significant colorization in the gel indicated that resorcinol and formaldehyde did not polymerize in an appreciable amount during this time. After sitting for one day, the gel shrank about 20% to provide an opaque red/orange gel with transparent yellow liquid around the gel. The gel was placed in an oven at 70° C. for 5 days after which the antimony-doped tin oxide gel was a hard opaque red/brown gel surrounded by clear light yellow liquid. After air drying for several days, the dried gels were burned in an electric heater for 1 to 2 minutes, then heated in a box furnace in air for 10 hours at 500° C. to produce a low-density dark-blue product with measurable conductance. The product kept the original shape and size upon visual inspection. A transmission electron micrograph of the product 1500 is shown in FIG. 15. The powder X-ray diffraction pattern of the product (sample 3b in FIG. 17) shows Bragg peaks that are assigned to antimony-doped tin oxide. The N$_2$ sorption isotherms and BJH pore distribution are shown in FIG. 18 and FIG. 19, respectively. The BET specific surface area was 81 m²/g with a pore volume of 0.27 cm³/g and an average pore size of 13.5 nm (4V/A by BET) (sample 3b). The UV-VIS diffuse reflectance spectrum for sample 3b is given in FIG. 20 together with some other samples after a Kubelka-Munk transformation was applied.

Figure 16:
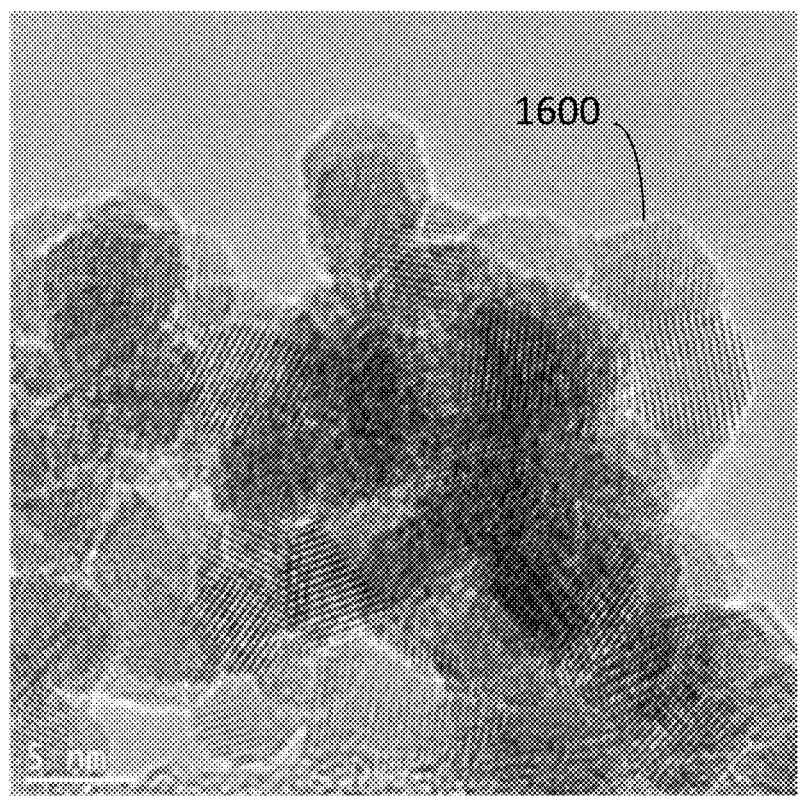
FIG. 16 is a transmission electron micrograph of porous antimony-doped tin oxide (sample 3c) formed by the method described in Example 3c.

Antimony-Doped Tin Oxide 2.8 g SnCl$_4$.5H$_2$O, 0.17 g SbCl$_3$, 1.0 g of resorcinol, and 1.48 g 37% formaldehyde solution were dissolved in 14.5 ml of a 50/50 v/v mixture of water and ethanol to produce the precursor solution at a pH of about 2. This mixture was placed in an ice-water bath with stirring for 10 minutes. 4.0 g of propylene oxide was added with stirring to the mixture while on the ice bath. The solution was stirred for about 90 seconds then removed from the ice bath. After this, the mixture gelled in about 1 minute. The gel was light yellow in color, which is associated with antimony/tin oxide gels prepared without organic polymer gel precursors. Lack of significant colorization in the gel indicated that resorcinol and formaldehyde did not polymerize in an appreciable amount during this time. After sitting for one day, the gel shrank about 20% to provide an opaque red/orange gel with transparent yellow liquid around the gel. The gel was placed in an oven at 70° C. for 5 days after which the antimony-doped tin oxide gel was a hard opaque red/brown gel surrounded by clear, light yellow liquid. After air drying for several days, the dried gels were burned in an electric heater for 1 to 2 minutes, then heated in a box furnace in air for 10 hours at 500° C. to produce a low-density, dark blue product with measurable conductance. The product kept the original shape and size upon visual inspection. A transmission electron micrograph of the product 1600 is shown in FIG. 16. The powder X-ray diffraction pattern of the product (sample 3c in FIG. 17) shows Bragg peaks that correspond to antimony-doped tin oxide. The $N_2$ sorption isotherms and BJH pore distribution are shown in FIG. 18 and FIG. 19, respectively. The BET specific surface area was 100 m$^2$/g with a pore volume of 0.28 cm$^3$/g and an average pore size of 11.0 nm (4V/A by BET) (sample 3c). The UV-VIS diffuse reflectance spectrum for sample 3c is given in FIG. 20 together with some other samples after a Kubelka-Munk transformation was applied.

Figure 21:
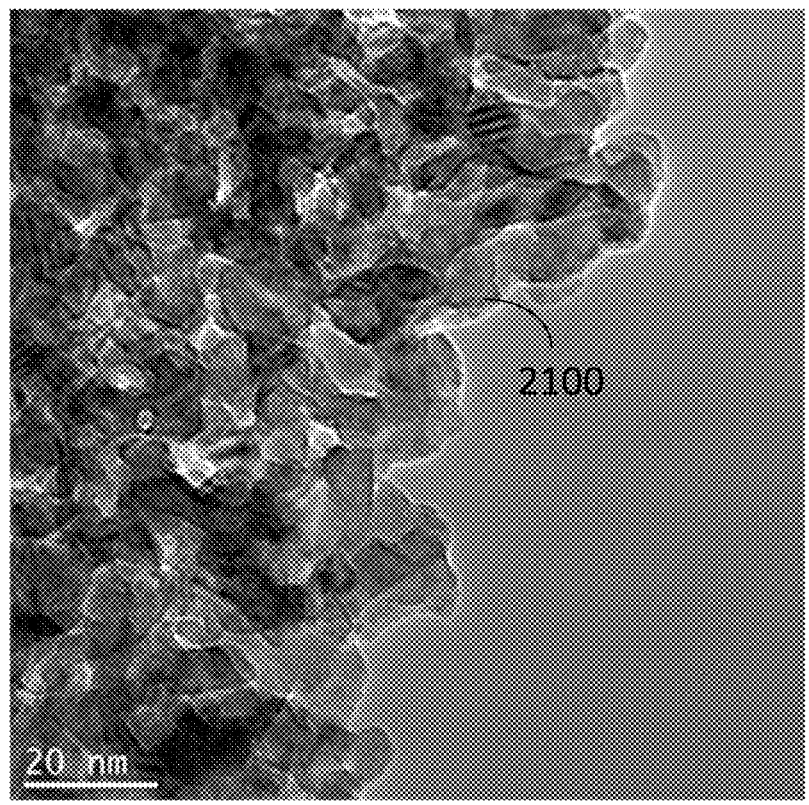
FIG. 21 is a transmission electron micrograph of porous yttria-stabilized zirconia (sample 4) formed by the method described in Example 4.
Figure 22:
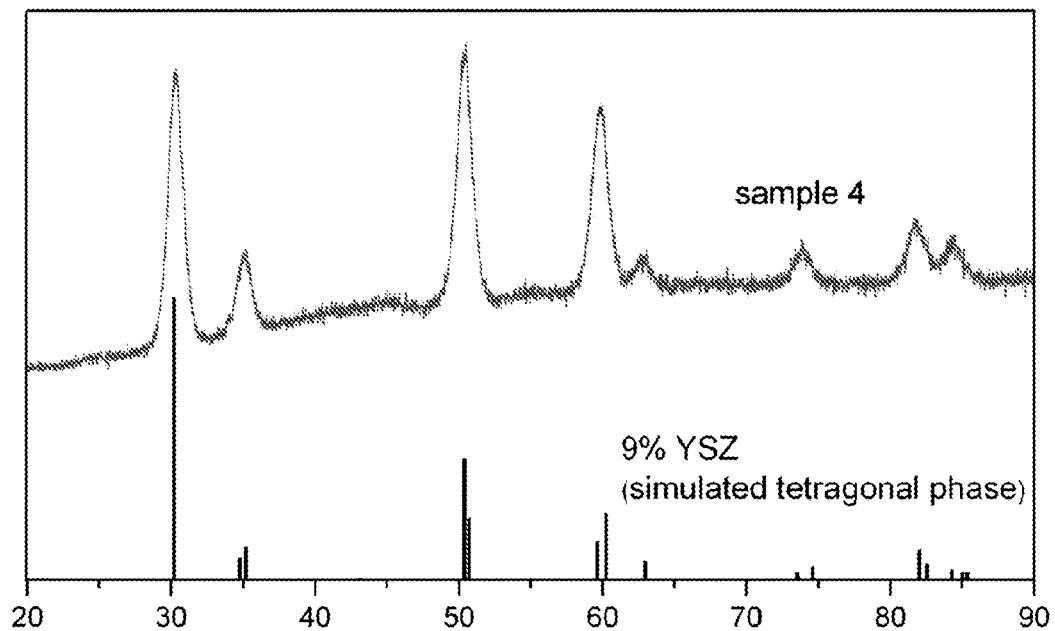
FIG. 22 is a powder X-ray diffraction pattern of porous yttria-stabilized zirconia (sample 4) formed by the method described in Example 4.
Figure 23:
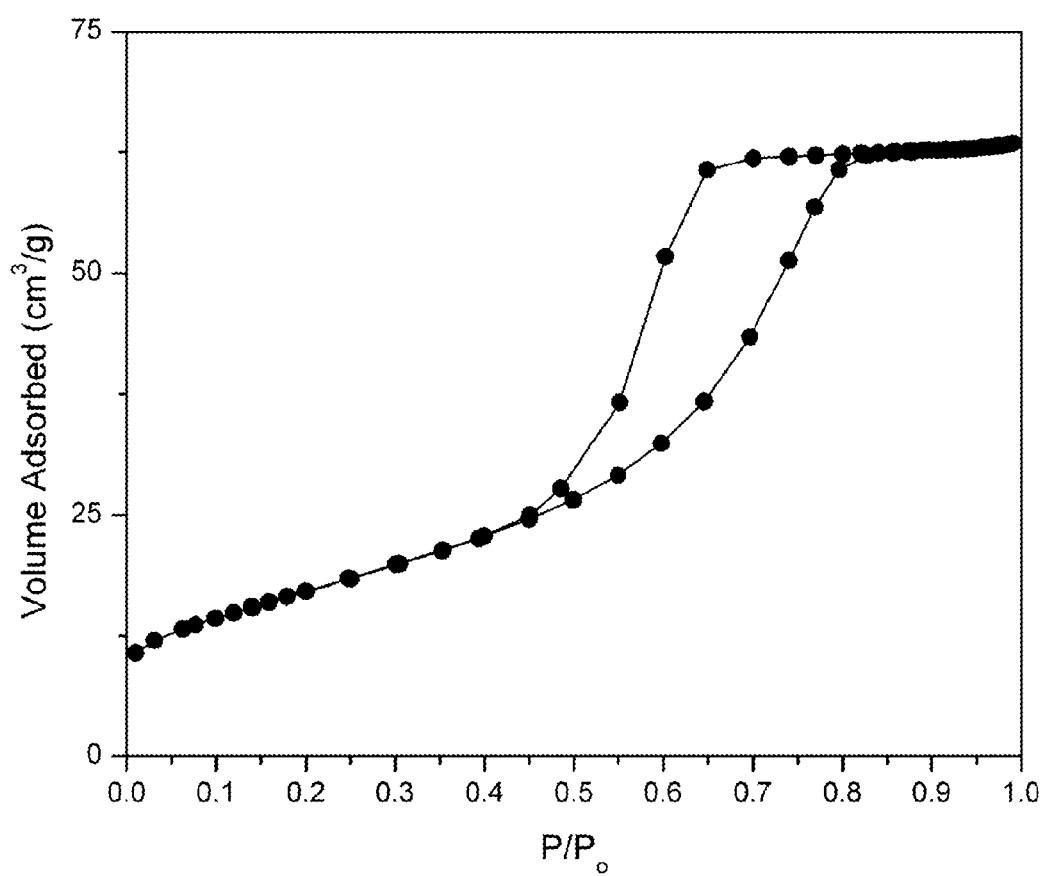
FIG. 23 is a $N_2$ sorption isotherm of porous yttria-stabilized zirconia (sample 4) formed by the method described in Example 4.
Figure 24:
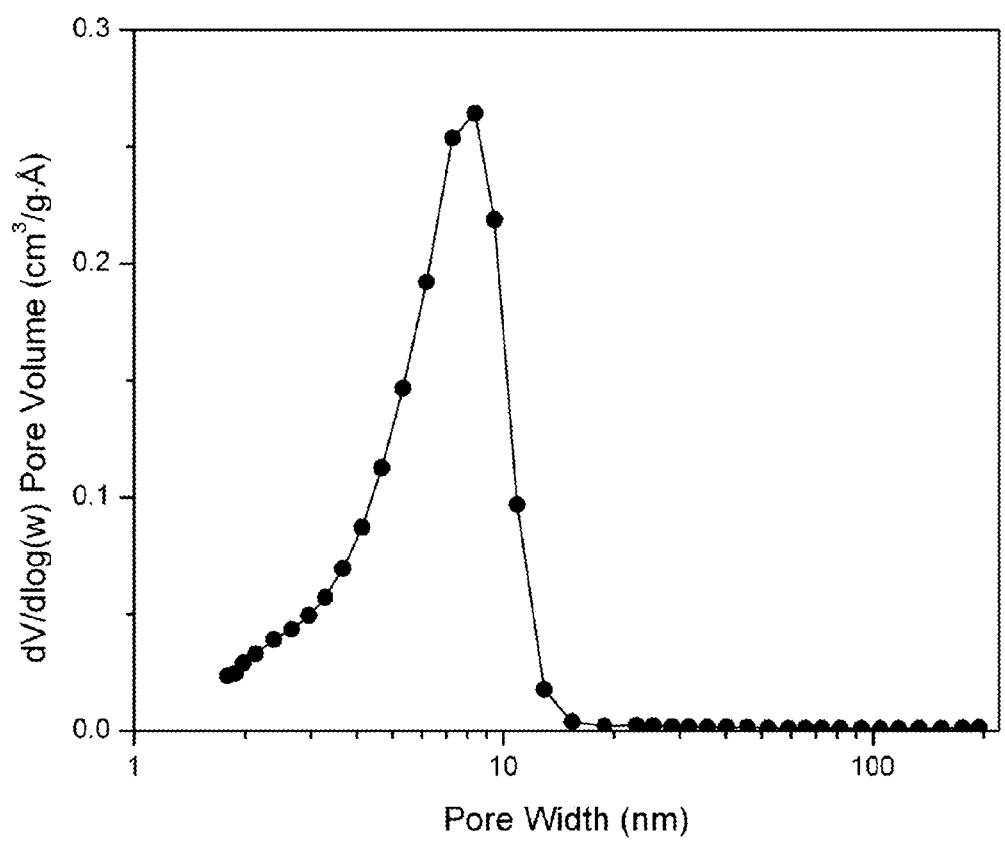
FIG. 24 is a BJH pore size distribution of porous yttria-stabilized zirconia (sample 4) formed by the method described in Example 4.

Yttria-Stabilized Zirconia 2.35 g ZrCl$_4$, 0.59 g YCl$_3$.xH$_2$O, 0.51 g resorcinol, and 0.75 g 37% formaldehyde solution were dissolved in 20 ml of a 50/50 v/v mixture of water and ethanol to produce the precursor solution at a pH of 1 to 2. This mixture was placed in an ice-water bath with stirring for 10 minutes. 5.0 g of propylene oxide was added with stirring to the mixture while on the ice bath. The solution was stirred for about 90 seconds then removed from the ice bath. After this, the mixture gelled in about 2 minutes. The gel was opaque and white, without indication of polymerization of resorcinol and formaldehyde. After sitting for one day, the gel shrank slightly to provide an opaque orange gel. The gel was placed in an oven at 70° C. for 1 day after which the yttria-stabilized zirconia gel was a hard opaque dark-red gel that shrank about 10%. After air drying for several days, the xerogels were heated in a tube furnace from room temperature to 110° C. at 2° C./min, held for 1 hour, then heated from 110 to 700° C. at 8° C./min and held for 1 hour all under flowing Ar. The composite particles were cooled to room temperature, moved to a box furnace and heated at 700° C. for 10 hours to produce a low-density, white product. The product kept the original shape and size upon visual inspection. A transmission electron micrograph of the product 2100 is shown in FIG. 21. The powder X-ray diffraction pattern of the product (FIG. 22) shows Bragg peaks that correspond to antimony-doped tin oxide. The $N_2$ sorption isotherms and BJH pore distribution are shown in FIG. 23 and FIG. 24, respectively. The BET surface area was 62.0 m$^2$/g with a pore volume of 0.10 cm$^3$/g and an average pore size of 6.3 nm (4V/A by BET) (sample 4).

Example 5

Figure 25:
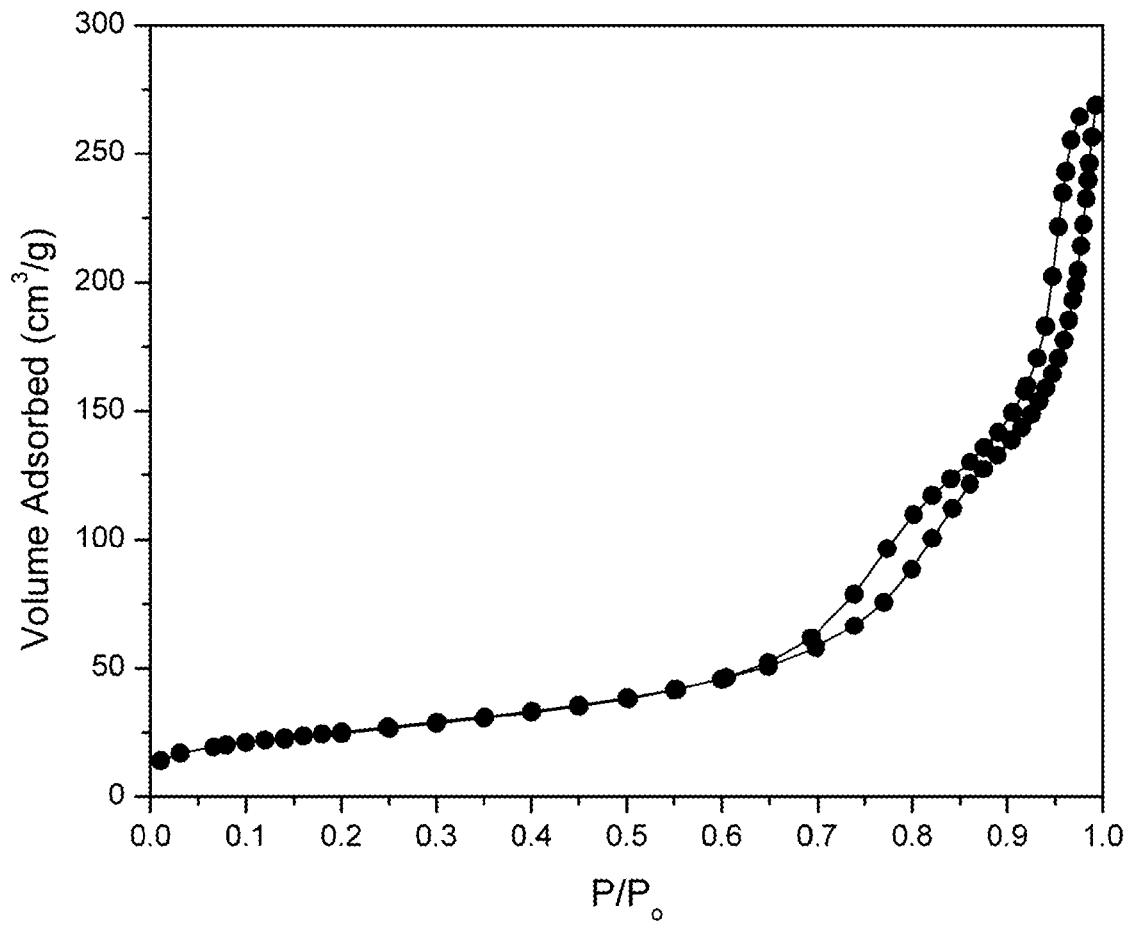
FIG. 25 is a $N_2$ sorption isotherm of porous antimony-doped tin oxide (sample 5) formed by the method described in Example 5.
Figure 26:
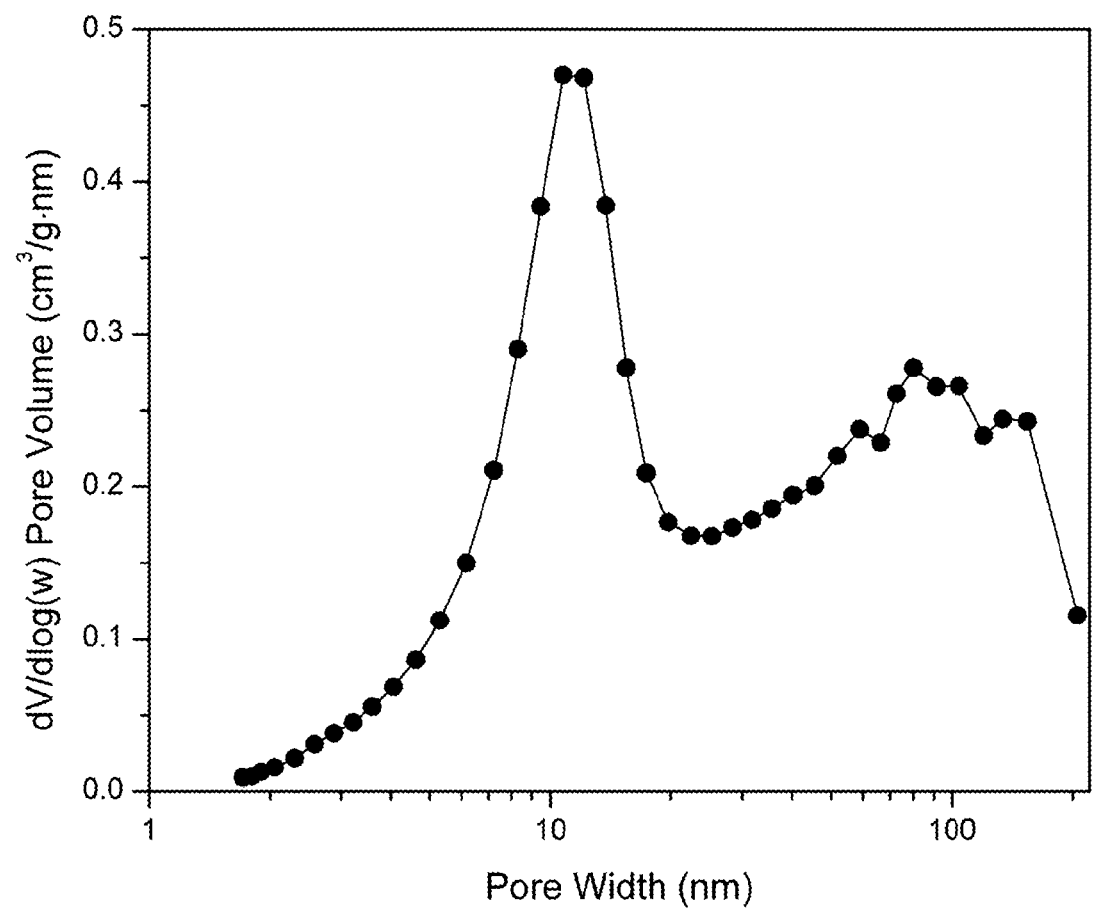
FIG. 26 is a BJH pore size distribution of porous antimony-doped tin oxide (sample 5) formed by the method described in Example 5.

Antimony-Doped Tin Oxide 0.28 g SnCl$_4$.5H$_2$O, 0.012 g SbCl$_3$, 0.151 g of polyethylene glycol (Fluka, MW~17,500), 0.099 g of resorcinol, and 0.158 g 37% formaldehyde solution were dissolved in 1.6 ml of a ~5/95 v/v mixture of water and ethanol to produce the precursor solution at a pH of about 2. Then 0.55 g of epichlorohydrin was added with stirring to the mixture. The solution was stirred for about 90 seconds then removed from stirring. After this, the mixture gelled after about 45 minutes. The gel was opaque and light yellow in color, which is associated with antimony/tin oxide gels prepared without organic polymer gel precursors. Lack of significant colorization in the gel indicated that resorcinol and formaldehyde did not polymerize in an appreciable amount during this time. After sitting for one day, the gel shrank about 20% to provide an opaque red/orange gel with transparent yellow liquid around the gel. The gel was placed in an oven at 70° C. for 2 days after which the antimony-doped tin oxide gel was a hard opaque red/brown gel surrounded by clear light yellow liquid. After air drying for several days, the dried gels were heated in a box furnace in air for 10 hours at 500° C. to produce a low-density dark-blue product with measurable conductance. The product kept the original shape and size upon visual inspection. The $N_2$ sorption isotherms and BJH pore distribution are shown in FIG. 25 and FIG. 26, respectively. The BET specific surface area was 92 m$^2$/g with a pore volume of 0.41 cm$^3$/g and an average pore size of 17.8 nm (4V/A by BET) (sample 5).

Only a few implementations are described and illustrated. Variations, enhancements and improvements of the described implementations and other implementations can be made based on what is described and illustrated in this document.

What is claimed is:

1. A method comprising:
    treating a precursor solution comprising an inorganic gel precursor, an organic polymer gel precursor, and a solvent to form an inorganic wet gel comprising an inorganic gel network, the organic polymer gel precursor, and the solvent, wherein the inorganic gel network comprises a metal oxide, a hydrous metal oxide, a metal hydroxide, or a combination thereof;
    treating the inorganic wet gel to form an interpenetrating inorganic-organic composite wet gel comprising an organic polymer network in the inorganic wet gel, wherein treating the inorganic wet gel comprises polymerizing the organic polymer gel precursor to form the organic polymer network in the inorganic wet gel, and wherein the inorganic gel network and the organic polymer network interpenetrate each other; and
    drying the composite wet gel to form a composite material comprising the organic polymer network and an inorganic network component comprising the metal oxide, the hydrous metal oxide, the metal hydroxide, or a combination thereof.

2. The method of claim 1, further comprising treating the composite material to form a porous composite material.

3. The method of claim 1, further comprising treating the composite material to remove at least some of the inorganic network component from the composite material, thereby yielding a porous polymer or a porous polymer composite.

4. The method of claim 3, wherein treating the composite material comprises etching out the inorganic network component with an acid or base, and dissolving or decomposing the inorganic network component.

5. The method of claim 1, further comprising heating the composite material with a sufficient amount of oxygen to remove the organic polymer network, thereby yielding a porous material comprising a porous metal oxide component substantially free from the organic polymer network.

6. The method of claim 1, further comprising heating the composite material in a limited oxygen environment to form a porous composite comprising the metal oxide and carbon.

7. The method of claim 6, further comprising heating the porous composite with a sufficient amount of oxygen to remove at least some of the carbon, thereby yielding a porous material comprising a porous metal oxide component.

8. The method of claim 7, wherein the porous metal oxide component is conducting or semi-conducting.

9. The method of claim 8, wherein the porous metal oxide component is a transparent conducting oxide.

10. The method of claim 6, further comprising treating the porous composite to remove the metal oxide, thereby yielding a porous carbon or porous carbon composite substantially free from the metal oxide.

11. The method of claim 10, wherein treating the porous composite comprises etching out the metal oxide with an acid or a base, and dissolving or decomposing the metal oxide.

12. The method of claim 2, further comprising removing a component from the porous composite material.

13. The method of claim 1, wherein the precursor solution comprises one or more additives selected from the group consisting of fibers, woven fibers, particles, carbon veils, carbon fibers, viscosity modifiers, and polymers.

14. The method of claim 1, wherein the inorganic gel precursor comprises one or more of a metal, semimetal, metalloid or semiconductor; inorganic salts; acid scavengers; epoxy-containing compounds; urea; organometallic compounds; and alkoxides of metals, semi-metals, metalloids, and semi-conductors.

15. The method of claim 1, wherein treating the precursor solution comprises heating the precursor solution to a temperature up to about 50° C.

16. The method of claim 1, wherein the organic polymer gel precursor comprises one or more of carbon-containing compounds, resorcinol, formaldehyde, phenol, polymerizable carbon-containing compounds, hydroxyl-substituted benzenes, urea, diamines, sugars, furfuryl alcohol, cellulose, and mesophase pitch.

17. The method of claim 1, wherein the inorganic wet gel comprises one or more of oxides, hydroxides, alkoxides, oxohydroxides, oxoalkoxides, oxo salts, or oxo salt hydrates of a metal, semi-metal, metalloid, or semi-conductor that acts as a solid acid catalyst or solid base catalyst for the organic polymer network.

18. The method of claim 1, wherein treating the inorganic wet gel comprises heating the inorganic wet gel to a temperature greater than about 50° C.

19. The method of claim 1, wherein the organic polymer gel precursor is polymerized to form the organic polymer network in the presence of an acid, a base, an oxidizing agent, a reducing agent, a base, or any combination thereof.

20. The method of claim 1, wherein the porous material is nanoporous or hierarchically porous or in the form of monoliths, films, plates, coatings, powders, particulates, or any combination thereof.

21. A material formed by the method of claim 1.

* * * * *